US012584101B2

(12) United States Patent
Frese

(10) Patent No.: US 12,584,101 B2
(45) Date of Patent: Mar. 24, 2026

(54) **COMPOSITIONS AND METHOD OF USE FOR H5 COMPETENT *BIFIDOBACTERIUM LONGUM* SUBSP. *INFANTIS***

(71) Applicant: INFINANT HEALTH, INC., Davis, CA (US)

(72) Inventor: Steven Frese, Oakland, CA (US)

(73) Assignee: INFINANT HEALTH, INC., Davis, CA (US)

( * ) Notice: Subject to any disclaimer, the term of this patent is extended or adjusted under 35 U.S.C. 154(b) by 0 days.

(21) Appl. No.: 18/371,651

(22) Filed: Sep. 22, 2023

(65) Prior Publication Data

US 2024/0271083 A1 Aug. 15, 2024

Related U.S. Application Data

(63) Continuation of application No. 17/059,928, filed as application No. PCT/US2019/034765 on May 30, 2019, now abandoned.

(60) Provisional application No. 62/730,511, filed on Sep. 12, 2018, provisional application No. 62/678,253, filed on May 30, 2018.

(51) Int. Cl.

| *A61K 35/745* | (2015.01) |
| *A61K 31/702* | (2006.01) |
| *A61K 35/747* | (2015.01) |
| *C12N 1/20* | (2006.01) |
| *C12N 1/205* | (2026.01) |
| *C12R 1/01* | (2006.01) |

(52) U.S. Cl.

CPC ............ *C12N 1/205* (2021.05); *A61K 31/702* (2013.01); *A61K 35/745* (2013.01); *C12R 2001/01* (2021.05)

(58) Field of Classification Search

CPC . C12N 1/205; C12N 1/04; C12N 1/38; A61K 31/702; A61K 35/745; A61K 9/19; A61K 9/28; A61K 9/48; A61K 45/06; C12R 2001/01

See application file for complete search history.

(56) References Cited

U.S. PATENT DOCUMENTS

| 9,855,302 B2 | 1/2018 | Gajewski |
| 11,318,175 B2 | 5/2022 | Kyle et al. |
| 2009/0098240 A1 | 4/2009 | Mills |
| 2010/0322904 A1 | 12/2010 | Scholtens |
| 2012/0171166 A1 | 7/2012 | Chow |
| 2013/0195803 A1 | 8/2013 | German et al. |
| 2017/0304375 A1 | 10/2017 | Kyle |

FOREIGN PATENT DOCUMENTS

| WO | 2009102199 A1 | 8/2009 | |
| WO | WO 2013123223 A1 * | 8/2013 | ............... C07K 7/06 |
| WO | 2016065324 A1 | 4/2016 | |
| WO | WO 2017156550 A1 * | 9/2017 | ........... A61K 35/745 |
| WO | 2019055718 A1 | 3/2019 | |

OTHER PUBLICATIONS

Bunesova et al. "Fucosyllactose and L-fucose utilization of infant *Bifidobacterium longum* and *Bifidobacterium kashiwanohense*," BMC Microbiology 16(248): 1-12 (2016).

Majta, et al. "Identification of Differentiating Metabolic Pathways between Infant Gut Microbiome Populations Reveals Depletion of Function-Level Adaptation to Human Milk in the Finnish Population," mSphere, 4(2): 1-11 (2019).

Odamaki et al. "Comparative Genomics Revealed Genetic Diversity and Species/Strain-Level Differences in Carbohydrate Metabolism of Three Probiotic Bifidobacteria Species." International Journal of Genomics, 2015 (567809): 1-12 (2015).

Alikhan et al. "BLAST Ring Image Generator (BRIG): simple prokaryote genome comparisons." BMC Genomics 12: 402 (2011).

Antipov et al. "hybridSPAdes: an algorithm for hybrid assembly of short and long reads." Bioinformatics 32(7): 1009-15 (2011).

Bankevich et al. "SPAdes: a new genome assembly algorithm and its applications to single-cell sequencing." J Comput Biol 19: 455-77 (2012).

Frese et al. "Persistence of Supplemented *Bifidobacterium longum* subsp. *Infantis* EVC001 in Breastfed Infants." mSphere 2(6): e00501-17 (2017).

Lawley et al. "Differentiation of *Bifidobacterium longum* subspecies longum and *Infantis* by quantitative PCR using functional gene targets." PeerJ 5: e3375 (2017).

Lee et al. "Quantification of carbohydrates in whey permeate products using high-performance anion-exchange chromatography with pulsed amperometric detection." J Dairy Sci 98(11): 7644-7649 (2015).

Lewis et al. "Maternal fucosyltransferase 2 status affects the gut bifidobacterial communities of breastfed infants." Microbiome 3:13 (2015).

Locascio el al. "Broad conservation of milk utilization genes in *Bifidobacterium longum* subsp. *Infantis* as revealed by comparative genomic hybridization." Annl Environ Microbiol. 76(22): 7373-81 (2010).

Scholz et al. "Strain-level microbial epidemiology and population genomics from shotgun metagenomics." Nat Methods 13(5): 435-438 (2016).

Seemann "Prokka: rapid prokaryotic genome annotation." Bioinformatics 30(14): 2068-69 (2014).

Sela et al. "The genonme sequence of Bifidabacteriun longum subsp. infantis reveals adaptatiens for miik utilization within the infam microbiome." PNAS, 105(48): 18964-69 (2008).

Smilowitz et al. "Safety and tolerability of *Bifidobacterium longum* subspecies *Infantis* EVC001 supplementation in healthy term breastfed infants: a phase I clinical trial." BMC Pediatrics 17: 133 (May 30, 2017).

(Continued)

*Primary Examiner* — Satyendra K Singh

(74) *Attorney, Agent, or Firm* — Nixon Peabody LLP; Mark J. FitzGerald; Alissa R. Young

(57) ABSTRACT

*Bifidobacterium longum* subsp. *infantis* comprising a functional H5 cluster, including the *Bifidobacterium longum* subsp. *infantis* EVC001 deposited under ATCC Accession No. PTA-125180 may be used in compositions for improving gut health in infants and adults.

18 Claims, 10 Drawing Sheets

Specification includes a Sequence Listing.

(56)  References Cited

OTHER PUBLICATIONS

Untergasser et al. "Primer3—new capabilities and interfaces." Nucleic Acids Res 40(15): e115 (2012).

Bin-Nun et al., "Oral probiotics prevent necrotizing enterocolitis in very low birth weight neonates." The Journal of pediatrics 147.2: 192-196 (2005).

Hoyos, "Reduced incidence of necrotizing enterocolitis associated with enteral administration of *Lactobacillus acidophilus* and *Bifidobacterium infantis* to neonates in an intensive care unit." International Journal of Infectious Diseases 3.4: 197-202 (1999).

Judge Jorge L. Alonso. "Memorandum Opinion and Order" in Evolve Biosystems, Inc., and the *Regents of the University of California*, v. *Abbott Laboratories* (Jan. 7, 2025).

Lin et al. "Oral probiotics reduce the incidence and severity of necrotizing enterocolitis in very low birth weight infants." Pediatrics 115(1): 1-4 (2005).

Interlocutory Decision in Opposition of EP Patent 3,209,308 (Jun. 6, 2025).

\* cited by examiner

1

COMPOSITIONS AND METHOD OF USE FOR H5 COMPETENT *BIFIDOBACTERIUM LONGUM* SUBSP. *INFANTIS*

CROSS REFERENCE TO RELATED APPLICATIONS

This application is a continuation under 35 U.S.C. § 120 of co-pending U.S. application Ser. No. 17/059,028, filed Nov. 30, 2020, which is a 35 U.S.C. § 371 National Phase Entry Application of International Application No. PCT/US19/34765, filed May 30, 2019, which designated the U.S., and which claims benefit under 35 U.S.C. § 119(e) of the U.S. Provisional Application No. 62/678,253, filed on May 30, 2018 and U.S. Provisional Application No. 62/730,511, filed on Sep. 12, 2018, the contents of each of which are incorporated herein by reference in their entireties.

SEQUENCE LISTING

The instant application contains a Sequence Listing which has been submitted in XML format via Patent Center and is hereby incorporated by reference in its entirety. Said XML copy, created on Sep. 2, 2025, is named 096910-192830USC1 SL.xml and is 2.842 bytes in size.

FIELD OF THE INVENTION

This invention relates generally to compositions and methods for selection of and use of *Bifidobacterium longum* subsp. *infantis* comprising a functional H5 gene cluster (genes required for successful colonization of the infant gut), including *Bifidobacterium longum* subsp. *infantis* EVC001 deposited under ATCC Accession No. PTA-125180 ("Deposited *Bifidobacterium*"). The *Bifidobacterium* may be formulated as a pharmaceutical composition, a food, a probiotic, or a combination thereof.

BACKGROUND

Human milk contains a significant quantity of complex oligosaccharides (HMO, which are up to 15% of total dry mass) in a form that is not usable as an energy source for the infant. Similar complex oligosaccharides found in the milk of all mammals are designated MMO herein. Certain microorganisms such as *Bifidobacterium longum* subsp. *infantis* (*B. infantis*) have the unique capability to consume oligosaccharides, such as those found in human or bovine milk. See U.S. Pat. No. 8,198,872 and U.S. Patent Application Publication No. 2013/0195803. *B. infantis* is an example of an organism that internalizes the HMOs before breaking them down. Other microbes, such as *B. bifidum*, break HMOs down extracellularly. When HMOs are available in the environment, binding proteins, transport systems, and enzymes to breakdown linkages within the oligosaccharides, are transcriptionally induced to change protein expression profiles.

*B. longum* subsp. *longum* and *B. longum* subsp. *infantis* diverged 5 million years ago. A genome analysis revealed that the ability to use HMO (*B. infantis*) vs not (*B. longum*) appeared to be reflected in genes found in 5 HMO clusters (H1-H5). The H1-H5 were proposed to be important for describing *B. infantis* nutritional preferences [LoCascio et al. *Appl Environ Microbiol* (2010) 76(22): 7373-81].

2

SUMMARY OF INVENTION

Composition with Bacteria Having H5 Gene Cluster; Amount of Bacteria

The invention provides a composition comprising a *Bifidobacterium longum* subsp. *infantis* comprising a functional H5 gene cluster and at least one oligosaccharide having a Type I or Type II core, where the H5 cluster comprises at least Blon_2175, Blon_2176, and Blon_2177, more typically where the functional H5 cluster comprises Blon_2171, Blon_2173, Blon_2174, Blon_2175, Blon_2176, Blon_2177, and galT. An organism with a functional H5 cluster will transport and consume LNB oligosaccharides. In one preferred mode if the invention, the *Bifidobacterium longum* subsp. *infantis* is *Bifidobacterium longum* subsp. *infantis* EVC001 deposited under ATCC Accession No. PTA-125180. The *Bifidobacterium* may be present in the composition of this invention at a concentration of from 1 million cfu/g to 500 billion cfu/g, and/or the *Bifidobacterium* may be present at a concentration of from 5 Billion cfu/g to 100 Billion cfu/g, and/or the *Bifidobacterium* may be present at a concentration of from 10 Billion cfu/g to 50 Billion cfu/g. Alternatively, the *Bifidobacterium* may be present in the composition at a concentration of from 50 million to 4 or 5 billion cfu/g.

Activated Bacteria—Functionality

Preferably, the *Bifidobacterium longum* subsp. *infantis* in the compositions of this invention is activated. In the compositions of this invention, the *Bifidobacterium* preferably contains a LNB transport system capable of internalizing one or more oligosaccharides before the oligosaccharide is hydrolyzed and is capable of hydrolyzing the internalized oligosaccharide, where the oligosaccharide has the structure of an oligosaccharide found in a mammalian milk, and the mammalian milk may be human, bovine, pig, rabbit, goat, sheep, camel milk, or mixtures thereof. Such *Bifidobacterium* will have a higher binding affinity to mammalian mucosal cells than Bifidobacteria of the same species cultivated in the absence of complex oligosaccharides.

Activated Bacteria—Gene Expression

Activated *Bifidobacterium* in the compositions of this invention typically comprise upregulated genes selected from the group consisting of Blon_0042, Blon_R0015, Blon_R0017, Blon_R0021, Blon_R0022, Blon_0879, Blon_0880, Blon_0881, Blon_0882, Blon_2177, Blon_2334, Blon_2335, Blon_2336, Blon_2337, Blon_2338, Blon_2339, Blon 2343, Blon_2344, Blon_2346, Blon_2347, and Blon_2331 and combinations thereof, and/or they comprise downregulated genes selected from the group consisting of Blon_0518, Blon_0785, Blon_2167, Blon_2168 and combinations thereof. Preferably, the activated *Bifidobacterium* expresses a gene coding for a sialidase or a fucosidase, and/or the *Bifidobacterium* expresses a gene coding for a sialic acid or a fucose transporter.

Activated Bacteria—Product-by-Process

The *Bifidobacterium* in the composition of this invention may be activated, because it has been cultured in the presence of at least one mammalian milk oligosaccharide. Alternatively, the *Bifidobacterium* may be activated by an activator, where the activator is from Table 4, which activator may be LNB or an activator that is an LNB oligosaccharide or otherwise is shown to upregulate; more preferably, the composition itself further comprises an LNB oligosaccharide.

Composition Plus Complex Oligosaccharides

The composition of this invention comprises oligosaccharides that require proteins expressed as part of the H5 cluster for their uptake and/or metabolism by *B. infantis*. These complex oligosaccharides have an LNB core structure, whether it is Type I or Type II (lacto-N-biose or N-acetyl lactosamine). Oligosaccharides having an LNB core structure may include galactose-N-acetyl galactosamine dimer (eg., β-D-Gal-(1→3)-D-GlcNAc); or more preferably any galactose-N-acetyl galactosamine trimer, (eg., Gal-(1→3)-D-GlcNAc-(1→3)-Gal, or Gal-(1→3)-D-GlcNAc-(1→4)-Gal, or Gal-(1→6)-D-GlcNAc-(1→4)-Gal, or Gal-(1→6)-D-GlcNAc-(1→3)-Gal) and derivatives thereof. The oligosaccharides which are part of the compositions of this invention are processed through the LNB-ABC transporter system on activated *B. infantis*.

In a preferred mode, the composition of this invention further comprises an isolated complex oligosaccharide, which may be in addition to the oligosaccharide having a Type I or Type II core. Typically, the complex oligosaccharide of the composition comprises a plurality of oligosaccharides with 2 to 10 residues (DP2-10 oligosaccharides) to include lacto-N-biose and N-acetyllactosamine. In these preferred embodiments, the complex oligosaccharide may be at least 20% of the weight of the composition, and/or the complex oligosaccharide may be at least 50% of the weight of the composition, and/or the complex oligosaccharide may be at least 80% of the weight of the composition. In some embodiments of this invention, the composition provides a total dietary intake of oligosaccharide in an amount of 0.001-100 grams per day, more preferably 1-20 grams, 3-20 grams or 5-10 grams per day, or optionally 10, 15, 20, 25, 30, 35, 40, 45, or 50 grams per day.

Oligosaccharides from MMO

The complex oligosaccharides in the compositions of this invention may include mammalian milk oligosaccharides (MMO), which may be isolated from a mammalian milk source or the structures identified in mammalian milk may be derived synthetically. The mammalian milk source may be human, bovine, pig, rabbit, goat, sheep, or camel milk. MMO in the compositions of this invention may comprise oligosaccharide molecules found in human milk oligosaccharides (HMO), bovine milk oligosaccharides (BMO), bovine colostrum oligosaccharides (BCO), goat milk oligosaccharides (GMO), or a combination thereof; particularly HMO. If the source is bovine, the bovine source may be from bovine milk, bovine colostrum, bovine colostrum concentrate, or mixtures thereof, where the bovine colostrum oligosaccharide may comprise any of Hex(4); Hex(4) HexNAc(2); or Hex(3) HexNAc(1) NeuAc(1) at levels greater than 1%, or the complex oligosaccharide may be from a milk processing stream such as whey permeate.

MMO particularly comprises lacto-N-biose (LNB), lacto-N-triose (LNT), at least one oligosaccharide having a Type I core, at least one oligosaccharide having a Type II core, and/or combinations thereof. Type I or type II may be isomers of each other. MMO typically includes one or more of lacto-N-biose (LNB), N-acetyl lactosamine, lacto-N-triose, lacto-N-neotriose, lacto-N-tetraose (LNT), lacto-N-neotetraose (LNnT), fucosyllactose (FL), lacto-N-fucopentaose (LNFP), lactodifucotetraose, (LDFT) sialyllactose (SL), disialyllacto-N-tetraose (DSLNT), 2'-fucosyllactose (2FL), 3'-sialyllactosamine (3SLN), 3'-fucosyllactose (3FL), 3'-sialyl-3-fucosyllactose(3S3FL), 3'-sialyllactose (3SL), 6'-sialyllactosamine (6SLN), 6'-sialyllactose (6SL), difucosyllactose (DFL), lacto-N-fucopentaose I (LNFPI), lacto-N-fucopentaose II (LNFPII), lacto-N-fucopentaose III (LNF-PIII), lacto-N-fucopentaose V (LNFPV), sialyllacto-N-tetraose (SLNT), their derivatives, or combinations thereof. Other type II cores include but are not limited to trifucosyllacto-N-hexaose (TFLNH), LNnH, lacto-N-hexaose (LNH), lacto-N-fucopentaose III (LNFPIII), monofucosylated lacto-N-Hexose III (MFLNHIII), Monofucosylmonosialyllacto-N-hexose (MFMSLNH).

Optionally, the complex oligosaccharide comprises at least one of (3Hex,4HexNac, 1 Fuc), (1Gal, 1GlcNAc, 1 NeuAc), or (1Glu, 1Gal, 1 NeuAc (3' or 6')), and/or the complex oligosaccharide is less than 50% fucosylated, and/or the complex oligosaccharide comprises one of the following ratios of constituents: 1) a ratio of Hex(2) NeuAc (1):Hex(2) HexNAc(1) less than 5.0; 2) a ratio of Hex(2) HexNAc(1):Hex (3) HexNAc(1) of greater than 1.0; 3) a ratio of Hex(2) HexNAc(1):Hex (3) HexNAc(2) of greater than 2.0; 4) a ratio of Hex(3):Hex (3) HexNAc(1) NeuAc(1) of less than 100; or 5) a ratio of Hex(2) HexNAc(1):Hex (4) NeuAc(2) NeuGc(1) of greater than 10. The fucosyllactose and/or sialyllactose may comprise 1-5% of the total oligosaccharides, 5-20% of the total oligosaccharides, or 20-50% of the total oligosaccharides, and/or the mass ratio of the complex oligosaccharide to the fucosyllactose and/or sialyllactose may be from 20:1 to 1:10. In one embodiment, the oligosaccharide is selected from 2FL, 3FL or one of its derivatives and the Type I or Type II core is optional.

Oligosaccharides from Plants

Alternatively, the complex oligosaccharide may be a plant-derived oligosaccharide, and the plant oligosaccharide may be from carrots, peas, broccoli, onions, tomatoes, peppers, rice, wheat, oats, bran, oranges, cocoa, olives, apples, grapes, sugar beets, cabbage, corn, or a mixture thereof, or the plant oligosaccharide may be from orange peels, cocoa hulls, olive pomace, tomato skins, grape pomace, corn silage, or a mixture thereof; typically the plant-derived oligosaccharides are between 2 and 10 sugar residues (DP2-DP10), between 3 and 10 sugar residues (DP3-DP10), between 5 and 10 sugar resides (DP5-DP10), or up to DP20. The plants oligosaccharides in some modes may mimic Type I or Type II activities. In other embodiments, they further comprise additional oligosaccharides. In an alternative mode, the oligosaccharide comprises galactooligosaccharide (GOS). The oligosaccharides may include: (a) include one or more Type II oligosaccharide core where representative species include LnNT; (b) one or more oligosaccharides containing the Type II core and GOS in 1:5 to 5:1 ratio; (c) one or more oligosaccharides containing the Type II core and 2FL in 1:5 to 5:1 ratio; (d) a combination of (a), (b), and/or (c); (e) include one or more Type I oligosaccharide core where representative species include LNT (f) one or more Type I core and GOS in 1:5 to 5:1 ratio; (g) one or more Type I core and 2FL in 1:5 to 5:1 ratio; and/or (h) a combination of any of (a) to (g) that includes both a type I and type II core.

Features of the Composition

The compositions may be in the form of a dry powder, a dry powder suspended in an oil, or as a solution, the dry powder may be spray dried or freeze-dried, and freeze-drying may be in the presence of a suitable cryoprotectant. The compositions of this invention may be in a powder with a water activity level of less than 0.35, less than 0.30, less than 0.25, less than 0.2, less than or less than 0.1, or the composition may be an anhydrous composition. In certain modes, the composition further comprises a cryoprotectant, and the cryoprotectant may be glucose, lactose, raffinose, sucrose, trehalose, adonitol, glycerol, mannitol, methanol, polyethylene glycol, propylene glycol, ribitol, alginate, bovine serum albumin, carnitine, citrate, cysteine, dextran, dimethyl sulphoxide, sodium glutamate, glycine betaine, glycogen, hypotaurine, peptone, polyvinyl pyrrolidone, or taurine, mammalian milk oligosaccharides, chitin, chitosan, other polysaccharides, or a combination thereof. Alternatively, the composition may be suspended in an oil, and the oil may be a medium chain triglyceride or other consumable oil. Alternatively, the composition may be a concentrated oligosaccharide syrup at least 57%. In syrup compositions that also include *Bifidobacterium* water activity is low enough to keep *Bifidobacterium* dormant.

Any of the compositions of this invention may further comprise a stabilizer, which may be a flow agent or a milk protein. The compositions may be in the form of a packet, sachet, orally disintegrating tablet, foodstuff, capsule, lozenge, effervescent tablet, suppository, enema, capsule, dry powder, dry powder suspended in an oil, chewable composition, syrup, or gel. Tablets or capsules may have an enteric coating, which may comprise one or more of fatty acids, waxes, shellac, plastics, plant fibers, methyl acrylate-methacrylic acid copolymers, cellulose acetate succinate, hydroxy propyl methyl cellulose phthalate, hydroxy propyl methyl cellulose acetate succinate, polyvinyl acetate phthalate (PVAP), methyl methacrylate-methacrylic acid copolymers, cellulose acetate trimellitate, sodium alginate, and zein.

The composition may be a pharmaceutical composition, dietary supplement, nutritional product, food product, probiotic, and/or prebiotic, and it may be formulated as a unit dose medicament.

Optional Functional Components of the Composition

In one mode, the composition further comprises a protein source rich in threonine, N-acetyl-threonine, gamma-glutamylthreonine, or a combination thereof.

In another mode, the composition according to this invention also comprises a secondary metabolite, which may be a short chain fatty acid, such as acetate, lactate, or combinations thereof.

In another mode, the composition may also include vitamins, such as vitamins A or D.

Methods of Using the Composition

This invention also provides a method of improving the health of a mammalian gastrointestinal tract comprising administering *Bifidobacterium* and oligosaccharide having a LNB core to a mammal in an amount and manner effective to affect the health of the gastrointestinal tract of the mammal. Such administration may comprise a therapeutically effective amount of any composition of this invention to a subject in need thereof. In the method of this invention, the improvement of the health of the mammal may be a reduction of colic in an infant, or the improvement of the health of the mammal is accelerating the development of the immune system in a baby, or the improvement of the health of the mammal is the result of the colonization of the GI tract of the baby with *B. infantis* at levels that represent more than 20% of the total gut microbiome as measured by fecal analysis.

Dosing to Colonize the GI Tract

The method of this invention provides for a method which comprises administering to a subject in need thereof a dose of *Bifidobacterium* and oligosaccharide having a LNB core, in an amount, and for a duration, wherein the population of *Bifidobacterium* is established in the gut of the subject. The method of this invention also provides for a method which comprises administering to a subject in need thereof a dose of *Bifidobacterium* and oligosaccharide having a LNB core, in an amount, and for a duration, wherein the population of *Bifidobacterium* is maintained in the gut of the subject. In some modes, the method of this invention further comprises monitoring the levels of the *Bifidobacterium* in the stools of the mammal. In particular, the invention provides a method of increasing the concentration of *Bifidobacterium* in the gastrointestinal tract of a mammal by administering an effective amount of any composition of this invention to a subject in order to increase levels of said administered *Bifidobacterium* in the feces of that mammal to greater than 10% of the total microbiome found in that feces, more preferably the increase of the levels of the administered *Bifidobacterium* in the feces of that mammal is greater than 20% of the total microbiome found in that feces, or greater than 50% of the total microbiome found in that feces, or even greater than 70% of the total microbiome found in that feces. Alternatively, utilization of MMO containing a lacto-N-biose core by the mammal may be used as a measure of colonization by *Bifidobacterium* according to this invention.

Dosing Both Bacteria and Complex Oligosaccharides

The method of this invention may further comprising administering to the subject a complex oligosaccharide, and the complex oligosaccharide and the *Bifidobacterium* may be provided either together or separately. For example, the complex oligosaccharide may be provided as a solution and the *Bifidobacterium* may be provided in dry form or as an enteric-coated tablet or capsule. Alternatively, the composition may be provided in a non-aqueous liquid or gel composition having both components and comprise complex oligosaccharide at a level of from about 1 g/L to 50 g/L. In the method of this invention, the complex oligosaccharide may make up at least 20% of the weight of the composition, more preferably at least 50% of the weight of the composition, even more preferably the complex oligosaccharide is at least 80% of the weight of the composition.

In the methods of this invention, the complex oligosaccharide may be administered prior to the administration of *Bifidobacterium*, or the complex oligosaccharide may be administered contemporaneously with the administration of *Bifidobacterium*, or the complex oligosaccharide may be administered after the administration of *Bifidobacterium*. In the method of this invention, the complex oligosaccharide is usually provided in a daily dose of from 1 to 20 grams, preferably from 1 to 10 grams, and the *Bifidobacterium* is usually provided in a daily dose of from 1 to 100 billion colony forming units (CFUs), preferably from 10 to 50 billion CFUs, and the subject in need thereof is administered a dose once daily or in multiple, optionally two, three, four, five, six, sub-doses administered at appropriate intervals throughout the day, and the composition is orally or rectally administered. Typically the composition is administered for at least 5 days, but may be provided as a single dose, preferably the composition is administered for a duration from 21 to 360 days. The composition of this invention may be administered for at least 10 days in order to maintain the levels of *Bifidobacterium* greater than at least 5% of the total fecal microbiome of the mammal, preferably greater than at least 20% of the total fecal microbiome of the mammal, more preferably greater than at least 50% of the total fecal microbiome of the mammal.

Source of Complex Oligosaccharides

In preferred modes, the complex oligosaccharides in the methods of this invention may include mammalian milk oligosaccharides (MMO), which may be isolated from a mammalian milk source or the structures identified in mammalian milk may be derived synthetically. The mammalian milk source may be human, bovine, pig, rabbit, goat, sheep, or camel milk. MMO in the compositions of this invention may comprise oligosaccharide molecules found in human milk oligosaccharides (HMO), bovine milk oligosaccharides (BMO), bovine colostrum oligosaccharides (BCO), goat milk oligosaccharides (GMO), or a combination thereof; particularly HMO. If the source is bovine, the bovine source may be from bovine milk, bovine colostrum, bovine colostrum concentrate, or mixtures thereof, where the bovine colostrum oligosaccharide may comprise any of Hex(4); Hex(4) HexNAc(2); or Hex(3) HexNAc(1) NeuAc(1) at levels greater than 1%, or the complex oligosaccharide may be from whey permeate.

MMO particularly comprises lacto-N-biose (LNB), lacto-N-triose (LNT), at least one oligosaccharide having a Type I core, at least one oligosaccharide having a Type II core, and/or combinations thereof. Type I or type II may be isomers of each other. MMO typically includes one or more of lacto-N-biose (LNB), N-acetyl lactosamine, lacto-N-triose, lacto-N-neotriose, lacto-N-tetraose (LNT), lacto-N-neotetraose (LNnT), fucosyllactose (FL), lacto-N-fucopentaose (LNFP), lactodifucotetraose, (LDFT) sialyllactose (SL), disialyllacto-N-tetraose (DSLNT), 2'-fucosyllactose (2FL), 3'-sialyllactosamine (3SLN), 3'-fucosyllactose (3FL), 3'-sialyl-3-fucosyllactose(3S3FL), 3'-sialyllactose (3SL), 6'-sialyllactosamine (6SLN), 6'-sialyllactose (6SL), difucosyllactose (DFL), lacto-N-fucopentaose I (LNFPI), lacto-N-fucopentaose II (LNFPII), lacto-N-fucopentaose III (LNFPIII), lacto-N-fucopentaose V (LNFPV), sialyllacto-N-tetraose (SLNT), their derivatives, or combinations thereof. Other type II cores include but are not limited to trifucosyllacto-N-hexaose (TFLNH), LNnH, lacto-N-hexaose (LNH), lacto-N-fucopentaose III (LNFPIII), monofucosylated lacto-N-Hexose III (MFLNHIII), Monofucosylmonosialyllacto-N-hexose (MFMSLNH).

Optionally, the complex oligosaccharide comprises at least one of (3Hex,4HexNac, 1 Fuc), (1Gal, 1GlcNAc, 1 NeuAc), or (1Glu, 1Gal, 1 NeuAc (3' or 6')), and/or the complex oligosaccharide is less than 50% fucosylated, and/or the complex oligosaccharide comprises one of the following ratios of constituents: 1) a ratio of Hex(2) NeuAc (1):Hex(2) HexNAc(1) less than 5.0; 2) a ratio of Hex(2) HexNAc(1):Hex (3) HexNAc(1) of greater than 1.0; 3) a ratio of Hex(2) HexNAc(1):Hex (3) HexNAc(2) of greater than 2.0; 4) a ratio of Hex(3):Hex (3) HexNAc(1) NeuAc(1) of less than 100; or 5) a ratio of Hex(2) HexNAc(1):Hex (4) NeuAc(2) NeuGc(1) of greater than 10. The fucosyllactose and/or sialyllactose may comprise 1-5% of the total oligosaccharides, 5-20% of the total oligosaccharides, or 20-50% of the total oligosaccharides, and/or the mass ratio of the complex oligosaccharide to the fucosyllactose and/or sialyllactose may be from 20:1 to 1:10. The complex oligosaccharide optionally contains at least one mannose residue, or at least one fucose or sialic acid residue. In some embodiments, the LNB oligosaccharide composition may also comprise a fucosyllactose and/or sialyllactose or derivatives of these compounds Alternatively, the complex oligosaccharide may be a plant-derived oligosaccharide, and the plant oligosaccharide may be from carrots, peas, broccoli, onions, tomatoes, peppers, rice, wheat, oats, bran, oranges, cocoa, olives, apples, grapes, sugar beets, cabbage, corn, or a mixture thereof, or the plant oligosaccharide may be from orange peels, cocoa hulls, olive pomace, tomato skins, grape pomace, corn silage, or a mixture thereof; typically the plant-derived oligosaccharides are between 2 and 10 sugar residues (DP2-DP10), between 3 and 10 sugar residues (DP3-DP10), between 5 and 10 sugar resides (DP5-DP10), or up to DP20. In an alternative mode, the oligosaccharide comprises galactooligosaccharide (GOS). The oligosaccharides may include: (a) include one or more Type II oligosaccharide core where representative species include LnNT; (b)

one or more oligosaccharides containing the Type II core and GOS in 1:5 to 5:1 ratio; (c) one or more oligosaccharides containing the Type II core and 2FL in 1:5 to 5:1 ratio; (d) a combination of (a), (b), and/or (c); (e) include one or more Type I oligosaccharide core where representative species include LNT (f) one or more Type I core and GOS in 1:5 to 5:1 ratio; (g) one or more Type I core and 2FL in 1:5 to 5:1 ratio; and/or (h) a combination of any of (a) to (g) that includes both a type I and type II core.

Target Population

The subject receiving the composition of this invention is a mammal which may be human, a cow, a pig, a rabbit, a goat, a sheep, a cat, a dog, a horse, or a camel; in a preferred mode, the mammal is a human infant, optionally the infant was delivered via cesarean section, or the infant was delivered vaginally, infant born preterm, \or the infant is 0-3 months, 3-6 months, 6-12 months, birth to weaning age. The compositions may be used in infants during weaning, for colic, or to normalize stool patterns. The composition may be used to change the *Bifidobacterium* composition of the gut by at least 0.5 or more preferably at least 1 log, and most preferably at least 2 log of any mammal in need of pathogen or potential pathogen reduction. Alternatively, the human is a pregnant woman, optionally, the pregnant woman is in at least the third trimester of pregnancy. In some modes, the infant is being fed with infant formula which contains no appreciable quantity of mammalian milk oligosaccharides, or the infant is nursed by a mother who is FUC-2 deficient as measured by a genetic test or the absence of complex fucosylated oligosaccharides in her milk.

Method of Making Activated Bacteria Having H5 Gene Cluster

This invention also provides a method of preparing activated *Bifidobacterium* comprising cultivating *Bifidobacterium* by incubating the *Bifidobacterium longum* subsp. *infantis* comprising a functional H5 cluster, including the *Bifidobacterium longum* subsp. *infantis* EVC001 deposited under ATCC Accession No. PTA-125180, under conditions whereby gene Blon_0042 is upregulated, gene Blon_2168 is downregulated, or combinations thereof. Alternatively, this invention provides a method of preparing activated *Bifidobacterium* comprising cultivating *Bifidobacterium* by incubating the *Bifidobacterium longum* subsp. *infantis* comprising a functional H5 cluster, including the *Bifidobacterium longum* subsp. *infantis* EVC001 deposited under ATCC Accession No. PTA-125180, under conditions whereby any of the genes Blon 0881, Blon_2334, Blon_2335, Blon_2336, Blon_2337, Blon_2338, Blon_2339, Blon 2343, Blon_2344, Blon_2346, Blon_2347, and Blon_2331, BLON 2175, BLON 2176, BLON 2175 is upregulated.

Culture in the Presence of MMO

This invention provides a method of preparing activated commensal *Bifidobacterium longum* subsp. *infantis* EVC001 deposited under ATCC Accession No. PTA-125180 comprising culturing this bacterial sp. in the presence of mammalian milk oligosaccharides (MMO), which may be isolated from a mammalian milk source or the structures identified in mammalian milk may be derived synthetically. The mammalian milk source may be human, bovine, pig, rabbit, goat, sheep, or camel milk. MMO in the compositions of this invention may comprise oligosaccharide molecules found in human milk oligosaccharides (HMO), bovine milk oligosaccharides (BMO), bovine colostrum oligosaccharides (BCO), goat milk oligosaccharides (GMO), or a combination thereof. Culture in the presence of MMO according to this invention will also maintain the functional H5 gene cluster in the genome of the *Bifidobac-*

*terium* strain, thereby producing cells that may be recovered as an inoculum for preparing *Bifidobacterium* having a functional H5 cluster for use in the therapeutic methods of this invention.

Culture in the Presence of Activators

In a preferred mode, this invention provides a method of preparing activated commensal *Bifidobacterium longum* subsp. *infantis* EVC001 deposited under ATCC Accession No. PTA-125180 comprising culturing said bacterial sp. in the presence of an activator selected from the compounds listed in Table 4, where bacterial cells in the culture medium are activated by the presence of the activating compound added to the medium. Preferably, the compound from Table 4 is added in an amount sufficient to induce expression of a gene and/or a protein encoding for a sialidase, a fucosidase, or an alpha-N-acetylgalactosaminidase, or genes listed in Table 1 or Table 2 in the bacterial cells, more preferably the activator is added to the culture medium in sufficient amounts to increase enzymatic activity of a fucosidase, sialidase, or alpha-N-acetylgalactosaminidase. The starting medium composition for cultures according to this invention may comprise one or more compounds from Table 4 in an amount from 0.1 to 3% by weight/vol of the media composition. The activator according to this invention may constitute a carbon source, and consumption of the carbon source by *Bifidobacterium* cells may both increase cellular biomass and activate a transport system capable of internalizing one or more oligosaccharides before the oligosaccharide is hydrolyzed and consequently the *Bifidobacterium* cells are further capable of hydrolyzing the internalized oligosaccharide, wherein the oligosaccharide has the structure of an oligosaccharide found in a mammalian milk, which may be human, bovine, pig, rabbit, goat, sheep, camel, or buffalo milk, or mixtures thereof.

Effect of Culture with Activators

Activated bacterial cells prepared according to this invention have a higher binding affinity to mammalian mucosal cells than bacterial cells of the same species cultivated on non-activating monomers or dimers. Such activated bacterial cells exhibit upregulated Blon_0881 and Blon_2343 in *B. infantis* or upregulation of the functional homologs in other bacterial species, the homologs being expressed during activation of the other bacterial species. *B. infantis* cells activated according to this invention exhibit upregulated amounts of glucosamine-6-phosphate isomerase and carbohydrate ABC transporter membrane protein from *B. infantis*. Activation of the *Bifidobacterium* cells according to this invention comprises upregulating the genes selected from the group consisting of Blon_0042, Blon_R0015, Blon_R0017, Blon_R0021, Blon_R0022, Blon_2177 and combinations thereof, and/or downregulating genes selected from the group consisting of Blon_0518, Blon_0785, Blon_2167, Blon_2168 and/or Blon_2177 gene from *B. infantis*. Alternatively, activation of the *Bifidobacterium* cells according to this invention comprises upregulating genes selected from the group consisting of Blon_0882, Blon_0881, Blon 0880, Blon_0879, Blon_2334, Blon_2335, Blon_2336, Blon_2337, Blon_2338, Blon_2339, Blon 2343, Blon_2344, Blon 2346, Blon_2347, Blon_2331, and combinations thereof.

DETAILED DESCRIPTION OF INVENTION

Figure 1:
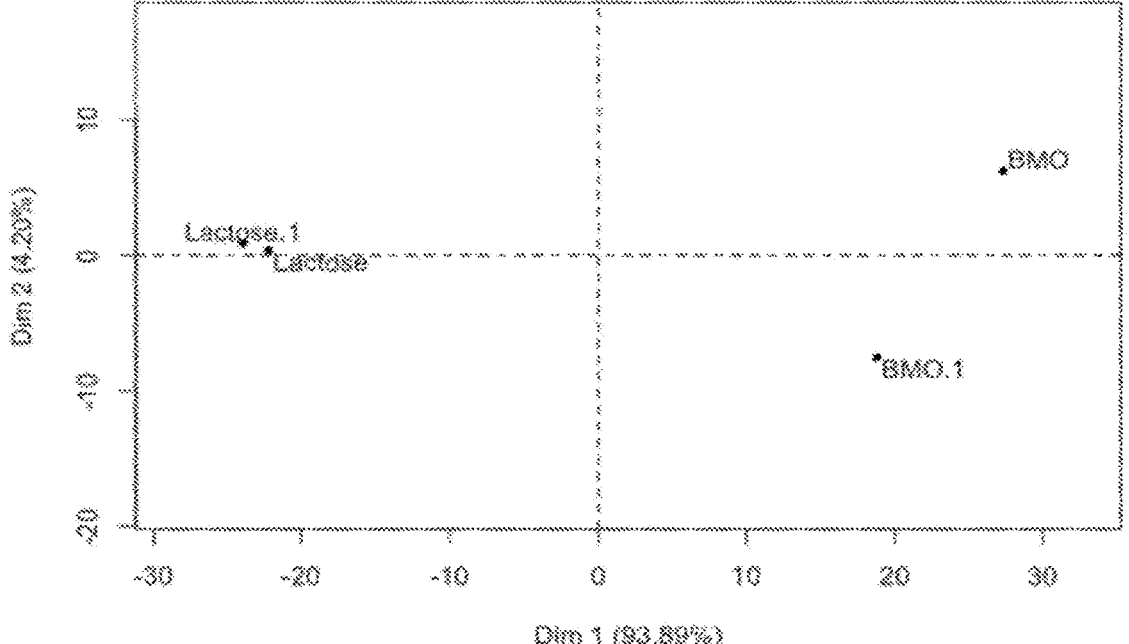
FIG. 1 is a diagram depicting whole genome expression analysis which shows differential gene expression of *B. infantis* cells grown in the presence of bovine milk oligosaccharides (BMO) or lactose.

An "activator," as used herein in, refers broadly to a commercial process where any monomeric or dimeric or an oligosaccharide greater DP3-20, or combinations of monomeric, dimeric carbohydrates and/or oligosaccharides capable of turning on one or more of the genes in Table 1, or in International application PCT/US2019/014097 or PCT/US2015/057226, related to HMO binding, transport or degradation or one or more of the genes in Table 2 related to NAG consumption. Examples of activators are listed in Table 4, International application PCT/US2019/014097. This invention can use, but is not limited to those activators listed in Table 4 or any MMO oligosaccharide listed in this application or PCT/US2015/057226.

Activation as used herein in, refers broadly to a change in gene expression for genes involved in consumption of MMOs, such as HMO or structurally related glycans, over the expression level in those same strains growth on lactose or glucose in a fermentation process. Genes involved in HMO function are defined as genes from the 5 HMO clusters defined in LoCascio, 2010 supra, whether or not they are actual found in those clusters. Activation may be determined as an increase in gene expression of specified genes and/or functional readouts of the encoded proteins such as sialidase or fucosidase or an alpha-N-acetylgalactosaminidase enzyme activity. Activation is measurable in the fermentation media and/or in the bulk dried concentrate and/or final product mixed with an excipient to dilute the product to the final concentration. The activated cell may show increased expression of solute binding proteins (SBP), extracellular enzymes, or ABC transporters on the cell surface or the change may be intracellular.

Activation occurs during production of the bacteria, which are dried in that state, examples of which are included in International Patent Application No. PCT/US2015/057226, filed Oct. 23, 2015, and International application PCT/US2019/014097, filed Jan. 18, 2019.

An activator is able to induce expression of genes in an organism but does not necessarily promote the selective growth of the organism over other organisms during an in vivo or an in vitro competition assay.

The total carbon source in the media will provide nutrients to support the exponential growth of the organism, or doubling time to produce a sufficient yield of activated product. The carbohydrates driving both rapid growth and activation may not come from the same molecules, but they can. The total carbohydrate/total carbon source for the type of fermentations covered by this invention will typically be in the range of 1-3% weight/volume or 10-30 g/L, but can be lower or higher. Residual sugars may be detectable in the spent media. A primary carbon source is one used to drive the yield, while the activator may be a primary carbon source, but its function is to change the gene expression. A primary carbon source plus an activator can equal the total carbohydrate or the total carbon source.

An "oligosaccharide," as used herein in, refers broadly to a carbohydrate having 3-20 sugar residues or degrees of polymerization from any source.

The "source of the oligosaccharide," as used herein refers broadly to oligosaccharides from animal, plant, fungi or algae that are free oligosaccharides, as well as those bound to animal or plant proteins or lipids (glycans), as well as those glycan structures after they are released from proteins or lipids or mixtures thereof.

The term "synthetic" composition refers to a composition produce by a chemi-synthetic process and can be nature-identical. For example, the composition can include ingredients that are chemically synthesized and purified or isolated. This does not include compositions that are naturally synthesized.

A "mammalian milk oligosaccharide (MMO)," as used herein in, refers broadly to an oligosaccharide from mammalian milk, whether it is purified or enriched or detectable in a dairy product, as long as the oligosaccharide is not subject to metabolism by digestive enzymes expressed in the mammalian genome. MMO includes individual structures synthesized to produce carbohydrate structures known to be in a mammalian milk including milk from human, bovine, equine, porcine, goat, camel, water buffalo, and sheep. An oligosaccharide regardless of its source (plant or animal) that functionally behaves as an MMO and can be mimicked by the monomer, dimer, or upstream or downstream metabolic intermediate covered by the invention of International application PCT/US2019/014097. The term "mammalian milk oligosaccharide" or MMO, as used herein, refers broadly to those indigestible glycans, sometimes referred to as "dietary fiber", or the carbohydrate polymers that are not hydrolyzed by the endogenous mammalian enzymes in the digestive tract (e.g., the small intestine) of the mammal. Mammalian milks contain a significant quantity of MMO that are not usable directly as an energy source for the milk-fed mammal but may be usable by many of the microorganisms in the gut of that mammal.

In some embodiments, the oligosaccharides are purified from human or bovine milk/whey/cheese/dairy products, (e.g., purified away from oligosaccharide-degrading enzymes in bovine milk/whey/cheese/dairy products). Purification of the oligosaccharide can mean separating a component of milk from any other components or otherwise processing mammalian milk including expressing human milk to provide for example the foremilk which is partially skimmed, human donor milk, or other human milk products such as fortifiers to use as colonization factors for *B. infantis* with the H5 cluster.

A "LNB oligosaccharide" contains a lacto-N-biose moiety that is core to the oligosaccharide or may be a entity itself. It may be in a type I or Type II core configuration, meaning a beta 1-3 or beta 1-4, respectively. N-acetyl lactosamine is an example of a type II entity. LNnT is a larger oligosaccharide structure that contains the Type II core. An example of a type I core is LNT. A visual representation of the different HMO structures including a description of a Type I and Type II core is provided in Bode "Human milk oligosaccharides: Every baby needs a sugar mama." *Glycobiology* (2012) 22(9): 1147-1162.

The core structures of HMO consist of lactose at the reducing ends elongated by $\beta$-1-3-linked lacto-N-biose I (LNB, Gal$\beta$1-3GlcNAc) and/or $\beta$-1-3/6)-linked N-acetyl-lactosamine (LacNAc, Gal$\beta$1-4GlcNAc). These core structures can be further elongated with residues of galactose (Gal), N-acetylglucosamine (GlcNAc), N-acetylneuraminic acid (Neu5Ac) and decorated with fucose or sialic acid Ninonuevo, et al. (2006). J Agric Food Chem 54 7471-7480. The combinatorial effect of elongation, fucosylation and sialyation produces a heterogenous mix of short-chain, long-chain and branched structures with more than 200 distinct HMO types identified to date [Kirmiz, et al. (2018). Annu Rev Food Sci Technol 9: 429]. Further, the high abundance of HMO and the predominance of type 1 structure over the type 2 structure [Advances in Nutrition 3: 473S (Urashima et al., 2012)], a trait unique to human milk, suggests an adaptation for structure specific-functions (i.e. type 1 HMO) [Ninonuevo, et al. (2006). J Agric Food Chem 54 7471-7480; Tao, et al. (2011) J Proteome Res 10(4), 1548-1557]. The type 1 tetrasaccharide Lacto-N-tetraose is one of the most highly abundant oligosaccharides in breast milk and together with its isomer Lacto-N-neotetraose (LNnT) and derivatives comprise up to 70% of the total amount of HMO [Ninonuevo, et al. (2006). J Agric Food Chem 54 7471-7480.]

An oligosaccharide that is useful in this invention for colonization is able to promote the selective growth of *B.*

*infantis.* More preferably, it is able to promote the selective growth of a *B. infantis* with a functional or competent H5 cluster.

*Bifidobacterium longum* subsp. *infantis* EVC001 was deposited under ATCC Accession No. PTA-125180; cells were deposited with the American Type Culture Collection at 10801 University Blvd, Manassas, VA 20110 under the Budapest Treaty on the International Recognition of the Deposit of Microorganisms for the Purposes of Patent Procedure.

Additionally, "Deposited Bacteria," as used herein, refers to the isolated *Bifidobacterium longum* subsp. *infantis* EVC001, deposited with the ATCC and assigned Accession Number, and variants thereof, wherein said variants retain the phenotypic and genotypic characteristics of said bacteria and wherein said bacteria and variants thereof have LNT transport capability and comprise a functional H5 gene cluster comprising BLON2175, BLON2176, and BLON2177.

The term "Bifidobacteria" and its synonyms refer to a genus of anaerobic bacteria having beneficial properties for humans. Bifidobacteria is one of the major taxonomic groups of bacteria that make up the gut flora; the bifidobacteria are among the beneficial bacteria that reside in the gastrointestinal tract and have health benefits for their hosts.

A "functional H5 cluster," refers to a cluster of genes in *Bifidobacterium* responsible for the uptake and metabolism of human milk oligosaccharides containing LNB. A functional H5 cluster comprises Blon_2175, Blon_2176, and Blon_2177. The H5 cluster comprises the following genes: Blon_2171, Blon_2173, Blon_2174, Blon_2175, Blon_2176, Blon_2177, and galT. Lacto-N-biose is a core dimer that is part of human milk oligosaccharide. It has been produced using a one pot enzymatic reaction to be used as a *bifidus* factor for growth in vivo (Biosci. Biotechnol. Biochem, 71 (8):2101-2104, 2007).

DETAILED DESCRIPTION OF PREFERRED EMBODIMENTS

The inventors discovered that there are 2 key lineages of *B. infantis.* One lineage has LNB-ABC transporter genes within one of the HMO clusters (H5) in their genomes, but others are missing LNB-ABC genes. The presence of the LNB-ABC transporter system confers a selective advantage in vitro and in vivo. This feature of LNB transport can be used to differentiate the deposited strain *B. infantis* EVC001 (ATCC Accession No. PTA-125180 formerly ATCC SD-7035) from other *B. infantis* strains that would not be suitable for growth in an MMO rich environment. The ability to utilize all HMO is conferred or absent depending on the presence or absence specifically of BLON 2175-2177. This information can be used for strain identity, integrity and/or strain activation or colonization potential in vivo.

Commercial applications to maintain artificial selective pressure on the deposited strain to prevent genetic drift may require oligosaccharides with an LNB feature. Based on the activity of genes contained within the H5 cluster, strains selected and maintained for a functional H5 gene cluster will be more competitive in an MMO environment. Conversely, the absence of genes within the H5 cluster indicates strains that are not suitable to promote colonization in an LNB rich intestinal environment. A composition of the deposited strain can be administered optimally to a mammal in the presence of oligosaccharides with type I cores (a beta 1-3 linkage) or type II cores (a beta 1-4 linkage) to improve colonization. Certain monomers or dimers, or intact oligosaccharides alone or in combination may be added to commercial fermentations of the deposited strain to both activate MMO utilization pathways and as a nutrient carbon source. More generally, oligosaccharides containing 3-10 sugar residues are substrates known to activate this pathway, and monomers and/or dimers have only recently been found to induce expression of genes in this pathway.

HMOs can be found as free oligosaccharides (dietary glycans) or conjugated via glycosidic bonds to protein or lipids. The major HMOs in milk include lacto-N-tetraose (LNT), lacto-N-neotetraose (LNnT) and lacto-N-hexaose, which are neutral HMOs, in addition to fucosylated oligosaccharides such as 2-fucosyllactose (2FL), 3-fucosyllactose (3FL), and lacto-N-fucopentaoses I, II and III. Acidic HMOs include sialyl-lacto-N-tetraose, 3' and 6' sialyllactose (6SL). HMOs are particularly highly enriched in fucosylated oligosaccharides. U.S. Pat. No. 8,197,872.

The invention provides compositions of a *B. infantis* strain that contains a functional H5 cluster, more specifically contains functional gene, and/or gene product for BLON 2175, BLON 2176, and BLON 2177, preferably where the composition also comprises at least one Lacto-N-Biose containing moiety. More preferentially, a Lacto-N-biose (LNB) with a Beta 1-4 linkage such as N-acetyl-lactosamine, but that core also refered to as a type II core may be part of a larger oligosaccharide structure, such as LnNT. Compositions may include Type 1 cores. Compositions may include both a type I and a type II core.

This invention provides a method of maintaining strain genetic integrity and strain identification during fermentation regardless of final activation step. This invention also provides a method of preparing the *Bifidobacterium longum* subsp. *infantis* comprising a functional H5 gene cluster, including the Deposited *Bifidobacterium*, in activated form, the method comprising culturing the *Bifidobacterium longum* subsp. *infantis* comprising a functional H5 gene cluster, including the Deposited *Bifidobacterium*, in the presence of an activator selected from compounds described in International applications PCT/US2015/065323 or PCT/US2019/014097, incorporated by reference in their entirety herein.

*Bifidobacterium longum* subsp. *infantis* comprising a functional H5 gene cluster is capable of transporting LNB or an oligosaccharide that contains an LNB moiety as part of said oligosaccharide. Confirmation of the functional H5 cluster may rely on the presence of BLON2175, BLON2176, and/or BLON2177 genes, gene products, and/or gene activities. It may also include the activity of BLON 2173 and BLON 2174 that breaks LNB moities (N-acetyl-galactosaminidase). In other embodiments, the fermentation may include activation of the *Bifidobacterium* cells as previously described in International applications PCT/US2015/065323 or PCT/US2019/014097. These embodiments may comprises upregulating Blon_0881 and Blon_2343. In other embodiments, activation involves enhanced expression of glucosamine-6-phosphate isomerase and carbohydrate ABC transporter membrane protein from *B. infantis.* In still other embodiments, activation of the *Bifidobacterium longum* subsp. *infantis* comprising a functional H5 gene cluster, including the Deposited *Bifidobacterium*, cells comprises upregulating the genes selected from the group consisting of Blon_0042, Blon_R0015, Blon_R0017, Blon_R0021, Blon_R0022, Blon_2177 and combinations thereof, and/or downregulating genes selected from the group consisting of Blon_0518, Blon_0785, Blon_2167, Blon_2168 from *B. infantis.* In yet other embodiments, the *Bifidobacterium longum* subsp. *infantis* comprising a functional H5 gene cluster, including the Deposited *Bifidobacterium* cells, comprise an upregulated Blon_0042 gene from *B. infantis*. In still other embodiments, the *Bifidobacterium longum* subsp. *infantis* comprising a functional H5 gene cluster, including the Deposited *Bifidobacterium* cells, comprise a downregulated Blon_2168 gene from *B. infantis*. In yet other embodiments, activation of the *Bifidobacterium longum* subsp. *infantis* comprising a functional H5 gene cluster, including the Deposited *Bifidobacterium* cells, comprise upregulating expression of genes selected from the group consisting of Blon_0882, Blon_0881, Blon_0880, Blon_0879, Blon_2334, Blon_2335, Blon_2336, Blon_2337, Blon_2338, Blon_2339, Blon_2344, Blon_2346, Blon_2347, and Blon_2331. In yet other embodiments, gene expression of one or more genes from Table 1, International application PCT/US2019/014097, and/or protein expression or protein activity are monitored to determine activation. In some embodiments, expression of genes from Table 2, International application PCT/US2019/014097, are used to monitor activation.

In various embodiments, the activator is present in culture media of this invention in an amount sufficient to induce a gene coding for a sialidase or a fucosidase in the *Bifidobacterium*. In some embodiments, the activator is present in the culture medium in an amount of from 0.1 to 20% by weight of the starting composition, in particular embodiments, Lacto-N-biose may be present during fermentation and/or drying. In other embodiments, lacto-N-biose structures are detectable in the final product.

In some embodiments, the supernatant is separated from the biomass; in other embodiments, the activated supernatant is dried with the cells. In some embodiments, cells of the *Bifidobacterium longum* subsp. *infantis* comprising a functional H5 gene cluster, including the Deposited *Bifidobacterium*, are dried with MMO or other oligosaccharides, preferably N-acetyllactosamime, LnNT and other type II core oligosaccharides (beta 1-4) and/or Type I cores such as lacto-N-biose, LNT or other structures that have the Beta 1-3 linkages. In these or other embodiments, excipients may be added to the recovered biomass, and the excipients maybe an MMO or oligosaccharide. In some embodiments, the excipient contains Lacto-N-biose, fucosyllactose (FL) or derivatives of FL including but not limited to, lacto-N-fucopentose (LNFP) and lactodifucotetraose (LDFT), lacto-N-tetraose (LNT) and lacto-N-neotetraose (LNnT), sialyl lactose. It may also include lactose. This invention may also provide a composition comprising an activated *Bifidobacterium* and an activator from MMO or listed in International application PCT/US2019/014097.

Consequently, the proliferation of *Bifidobacterium longum* subsp. *infantis* comprising a functional H5 gene cluster, including the Deposited *Bifidobacterium*, in the gut of a newborn infant, triggered and uniquely enabled by the HMOs provided in mother's milk, is of significant benefit to the health and long term survival of that infant. Consequently, *Bifidobacterium longum* subsp. *infantis* comprising a functional H5 gene cluster, including the Deposited *Bifidobacterium*, provide significant benefits to a newborn infant which include, but are not limited to, a higher binding affinity to the gut mucosa, higher colonization of the GI tract thereby preventing growth of other bacterial clades, a higher production of short chain fatty acids, higher consumption of complex oligosaccharides, and a greater stimulation of the immune response as measured by positive alterations of immune response markers, relative to the organism in a pre-activated state. Lewis et al. (2015) *Microbiome* 3:13; Huda et al. (2014) *Pediatrics* 134:2 e362-e372.

With a functional H5 cluster, the *B. infantis* becomes the sole consumer of the human milk oligosaccharides (HMO) and has been shown to increase its relative proportion in the gut microbiota of infant humans to levels at least 10-fold higher than its levels at birth (prior to consumption of HMO), or in those infants exclusively fed commercial infant formula not containing milk glycans, and reaching levels as high as 70% of the total microbial population of the distal colon. When *B. infantis* is present in the gut of a baby, and that baby is also provided with its mother's milk as a sole source of nutrition, the population of *B. infantis* can increase to levels as high as 90% of the total bacterial population of the gut as measured by the microbial quantification of the stool. The activated *Bifidobacterium longum* subsp. *infantis* comprising a functional H5 gene cluster, including the Deposited *Bifidobacterium*, will remain in the gut at high concentrations and remain activated as long as a dietary source of the selective complex oligosaccharides (e.g., HMO to human babies) is provided to the mammal. Once the source of the complex oligosaccharides is withdrawn from the diet (e.g., at weaning), the *B. infantis* is no longer activated, it can no longer successfully compete with other gut microbiota for nutrients in the gut, and its population rapidly decreases to less than 1% of the total microbiome. *B. infantis* is not normally found in the gut of a weaned infant, child, or adult in levels of more than 1%.

Description of Genotypic Comparisions

Whole genome sequencing was used to compare a number of *B. infantis* strains. The H5 cluster was determined to be functionally relevant for use in applications that comprise oligosaccharides most preferentially containing the Type II core structure. The *B. infantis* genomes could be used to distinguish between those that have BLON 2175-BLON 2177 and those which do not. See FIGS. 2A-D. This information can be used to generate strain specific primers for detecting and monitoring strains in a complex environment. These are useful for strain indentity and monitoring strain integrity over time.

Description of the Activation Phenotype

In some embodiments, the activation phenotype involves upregulating one or more of the genes contained in one or more HMO gene clusters. Examples of these gene clusters from *B. infantis* are listed in Table 1. The function of the respective gene is the important part of the invention.

TABLE 1

List of genes that are associated with HMO consumption in
*B. infantis* as described in Locascio 2010 and Gerrido (2013)
Microbiology 159: 649-664. The prefix Blon refers to genes
in *B. longum* and *B. infantis*. *B. infantis* specific gene clusters

| H1 HMO cluster | H2 Fucosidase | H3 Fucosidase | H4 Sialic Acid | H5 Lacto-N-biose | Urease Cluster |
|---|---|---|---|---|---|
| Blon_2331 | Blon_0243 | Blon_0423 | Blon_0641 | Blon_2171 | Blon_0104 |
| Blon_2332 | Blon_0244 | Blon_0424 | Blon_0642 | Blon_2172 | Blon_0105 |
| Blon_2334 | Blon_0245 | Blon_0425 | Blon_0643 | Blon_2173 | Blon_0106 |
| Blon_2336 | Blon_0246 | Blon_0426 | Blon_0644 | Blon_2174 | Blon_0107 |
| Blon_2342 | Blon_0247 | | Blon_0645 | Blon_2175 | Blon_0108 |
| Blon_2343 | Blon_0248 | | Blon_0646 | Blon_2176 | Blon_0109 |
| Blon_2344 | | | Blon_0647 | Blon_2177 | Blon_0110 |
| Blon_2347 | | | Blon_0648 | | Blon_0111 |
| Blon_2348 | | | Blon_0649 | | Blon_0112 |
| Blon_2350 | | | Blon_0650 | | Blon_0113 |
| Blon_2351 | | | Blon_0651 | | Blon_0114 |
| Blon_2352 | | | | | Blon_0115 |
| Blon_2354 | | | | | |
| Blon_2355 | | | | | |
| Blon_2357 | | | | | |
| Blon_2359 | | | | | |
| Blon_2360 | | | | | |
| Blon_2361 | | | | | |

The presence of Blon_2177 (gene name: extracellular solute-binding protein, family); Blon_2176 (gene name: binding-protein-dependent transport systems inner membrane component); Blon_2175 (gene name: binding-protein-dependent transport systems inner membrane component) can be used to identify *B. infantis* strains with a functional H5 gene cluster.

The activation phenotype can relate to the capture, internalization and/or metabolism of the HMO; and/or relate to the binding affinity for epithelial cells; as well as catabolism of milk sugar monomers, dimers, or oligosaccharides; and/or production of tryptophan or indole derivatives. The activation phenotype can involve any inducible pathway that accompanies preparation of a stable, activated bacterial phenotype with an improved ability to consume fiber/oligosaccharides within the colon of an animal or human, where the oligosaccharides include but are not limited to oligosaccharides and/or other fiber, but may more particularly refer to MMO. This invention provides for production of the activation phenotype prior to consumption and/or use of oligosaccharides/fiber in said animal or human. In some cases, it is for a newborn infant of the said animal or human.

Activation may specifically include genes related to NAG consumption: Blon_0882 (N-acetylglucosamine 6-phosphate deacetylase (EC 3.5.1.25)), Blon_0881 (glucosamine-6-phosphate isomerase), Blon_0880 (NagC/XylR-type transciptional regulator), Blon_0879 (Sugar kinase of the NBD/HSP70 family) from *B. infantis*. (Table 2) Functional homologs of any of these genes from other species can be used to measure activation in their respective species.

TABLE 2

*B. Longum/B. infantis* genes associated with
NAG pathways that may represent activation.

| Gene | Function |
|---|---|
| Blon_0882 | N-acetylglucosamine 6-phosphate deacetylase (EC 3.5.1.25) |
| Blon_0881 | glucosamine-6-phosphate isomerase, |
| (Blon_0880 | NagC/XylR-type transciptional regulator |
| Blon_0879 | Sugar kinase of the NBD/HSP70 family |

TABLE 2-continued

*B. Longum/B. infantis* genes associated with
NAG pathways that may represent activation.

| Gene | Function |
|---|---|

In various embodiments, activation in *Bifidobacterium infantis* requires upregulation of Blon_0881 (glucosamine-6-phosphate isomerase) and Blon_2343 (carbohydrate ABC transporter membrane protein) and/or homologs of glucosamine-6-phosphate isomerase and carbohydrate ABC transporter membrane protein (Table 3), and activation can be confirmed by monitoring expression of these genes. In other embodiments, an additional gene is selected from one of the clusters listed in Table 1 or Table 2, or its functional homologues in other species. In some embodiments, activation is alternatively measured using one or more genes that are not Blon-0881 or Blon_2343 or its species-specific functional homologs. In some embodiments, activation of the HMO phenotype involves upregulation of a transcriptional regulator, such as Blon_0042 from *B. infantis*. In other embodiments, activation genes may be selected from one or more of Blon_R0015, Blon_R0017, Blon_R0021, Blon_R0022 transfer RNA (tRNA) of the amino acids valine, leucine, phenylalanine, and aspartate, respectively. In further embodiments activation may involve monitoring downregulation of Blon_0518, Blon_0785 (ABC-type nitrate/sulfonate/bicarbonate transport system, periplasmic component), Blon_2167 (hypothetical protein), Blon_2168 (phage shock protein C (PspC) family protein) alone or in addition to one or more genes that are also activated by the activation source selected from Table 4.

Table 1 and Table 2 describe the gene loci in *B. infantis* and the gene functions whose homologs can be found in other species that can reliably turn on part or all of the HMO phenotype (activation phenotype) and are the basis for describing activation in either *Bifidobacterium, Lactobacillus* and/or *Pediococcus*. In some embodiments, a Blon_2343 gene is selected from HMO cluster 1 and another gene marker of activation from a region outside one of the HMO clusters. Typically, a gene is also selected that is constitutively expressed within the organism to normalize the data. Table 3 shows a suitable set of genes for monitoring activation.

TABLE 3

List of Locus Tags for genes to determine activation using a constitutive reference gene from *B. infantis*. The reference gene normalizes the data.

| Locus Tag | Gene product | Gene Purpose |
| --- | --- | --- |
| Blon_0881 | glucosamine-6-phosphate isomerase or NAG B | Activation |
| Blon_2343 | carbohydrate ABC transporter membrane protein | Activation |
| Blon_0393 | cysteinyl-tRNA synthetase | Reference |

In some embodiments, activation is considered to be when the relative expression of the genes is upregulated compared to the same genes when the cell is grown on lactose or glucose. The genes selected for activation are known to be upregulated when grown in the presence of MMO compared to lactose or glucose, so if their expression is increased relative to the reference gene, it is sufficient to describe activation. In some embodiments, gene activation relates to Blon_0881 and Blon_2343 and their expression is greater than 1; that is, when the delta delta cycle threshold ($2^\wedge\Delta\Delta Ct$) is greater than 1, DDCT is calculated using Blon_0393, or another constitutively expressed gene as a reference. The result (activation) is the fold change ($2^\wedge\Delta\Delta Ct>1$) of gene expression. Determined based on the double delta CT ($2^\wedge\Delta\Delta Ct$) method (Livak K and Schmittgen T. (2001) Analysis of relative gene expression data using real-time quantitative PCR and the 2(−Delta Delta C(T)) Method. Methods: 25: 402-8). In other embodiments, other genes from Table 1 are used in addition to Blon_0881 and Blon_2343.

In other embodiments, a functional readout of activation is measured using sialidase and/or fucosidase and/or an alpha-N-acetylgalactosaminidase activity. In other embodiments, activation is determined by both gene activation and a functional readout. In some embodiments activation is monitored, using solute binding proteins or ABC transporters. In some embodiments, cell binding is monitored for activation.

Description of the Different Monomers and Dimers that can be Used to Activate Cells A selected group of monomers or dimers that includes, but is not limited to N-Acetyl glucosamine/galactosamine (NAG), dimers containing at least one moiety of NAG, fucose, and/or sialic acid, lacto-N-Biose, galacto-N-biose, hexose disaccharide (eg. Fuc $\alpha$1,2Gal$\beta$), may be used in fermentation processes according to this invention as activators of the MMO pathway(s), and optionally as a primary carbon source as described in International application PCT/US2019/014097. These activators are listed in Table 4.

TABLE 4

List of sources that can be used in this invention to act as activators alone or in combination to activate conditionally expressed oligosaccharide pathways Source N-acetyl-glucosamine/galactosamine (NAG)
Dimeric N-acetylglucosamine
Fucose
Sialic Acid

TABLE 4-continued

List of sources that can be used in this invention to act as activators alone or in combination to activate conditionally expressed oligosaccharide pathways Source Lacto-N-biose
Galacto-N-Biose
Fuc $\alpha$1,2Gal$\beta$ Working Stocks Generated Using LNB In some embodiments, the desired strains are selected on agar containing LNB and transfered to a liquid culture containing LNB as the sole carbon source. The cells are grown to the stationary phase, spun down and frozen with 15% glycerol. These stocks create the working stock or starter culture for large scale fermentation runs. Use of LNB as the sole carbon source provides selective pressure to avoid losing the H5 cluster to genetic drift. The large scale fermentation runs can use any carbon sources whether they activate or not to create the biomass.

Description of Fermentation Processes to Produce Activated *B. infantis*

In some embodiments, one or more of the sources listed in Table 4 can be used as the total carbon source required in the fermentation to increase the biomass of *Bifidobacterium* and activate the cells before they are harvested from a fermenter. In other embodiments, the sources listed in Table 4 are added as a percentage of the total carbohydrate added to the fermentation, e.g. 5%, 10%, 20%, 30%, 40%, 50%, 60%, 70%, 80% or 90%. While the remainder of the carbon source comes from glucose, galactose or lactose to make 100% of the carbon source at the beginning of the fermentation. In other embodiments, an activating compound (source) from Table 4 may be added to a fermentation during the late exponential phase to turn on the oligosaccharide pathway. In other embodiments the carbon sources listed in Table 4 are fed (supplied) to the fermenter intermittently or continuously via one or more feed streams during cultivation. In other embodiments, cells are re-suspended in a solution containing the sources in Table 4. In other embodiments, the cells are transferred to a secondary fermentation vessel containing the sources listed in Table 4.

In some embodiments, a composition of fermentation media is prepared that contains an activator as the sole carbon source (100% of the total carbohydrate present in the fermentation media). A fermentation typically will start with the carbon source (carbohydrate) at 1-3% of the final composition (weight/volume). In these embodiments, the activator may increase biomass or yield and turn on the right genes for HMO consumption before the cells are harvested.

In other embodiments, a composition of fermentation media is prepared that contains one or more simple fermentable sugars, such as glucose, galactose or lactose as the primary carbon source and an activator (i.e NAG, fucose, sialic acid or another compound listed in Table 4 are both added at the start of fermentation. The primary carbon source may be at least 90%, 85%, 80%, 75%, 70%, 65%, 60%, 55%, 50%, 45%, 40%, 35%, 30%, 25%, 20%, 15%, 10%. The remainder of the carbon source may be the activator at 10%, 15%, 20%, 25%, 30%, 35%, 40%, 45%, 50%, 55%, 60%, 65%, 70%, 75%, 80%, 85%, 90% of the total carbohydrate present (carbon source) in the starting media.

When a composition that contains a simple fermentable sugar, such as glucose, galactose or lactose as the primary carbon source is used to initiate the fermentation and contains up to 50%, 60%, 70%, 80%, 90% or 100% of the required carbon for the size of fermentation being conducted. Then the activator is added during the late exponential phase when a simple fermentable sugar is reduced from the starting levels. The activator (i.e NAG or any of the other sugars listed in Table 4) is added in late exponential phase to be 5%, 10%, 15%, 20%, 25%, 30%, 35%, 40%, 45%, 50%, 55%, 60%, 65%, 70%, 75%, 80, 85%, 90%, 95%, 100% of the amount of total carbohydrate present at the start of the fermentation. The activating compound from Table 4 may be left over in the spent media and dried with the organism or it may be completely used before the cells are harvested.

A method of preparing/priming/activating the *Bifidobacterium longum* subsp. *infantis* comprising a functional H5 gene cluster, including the Deposited *Bifidobacterium*, to have the enzymes produced that are necessary to consume HMO prior to being put into a dormant state. Any of the compositions described herein may be prepared by cultivating a bifidobacteria in an axenic culture (e.g., a culture with genetic homogeneity), and the culture will become "activated" if one or more of the compounds listed in Table 4 are included in the medium. In various embodiments, any of the compositions described herein can be made by isolating bifidobacteria; purifying the bacteria; inoculating a fermenter with the purified strains of the bifidobacteria; culturing the bifidobacteria in the presence of one or more activators from Table 4; and harvesting the cells. Fermentations for bifidobacteria may be carried out in stirred tank fermenters of commercial volume (e.g., 1-500 m$^3$) which are maintained under anaerobic conditions throughout the fermentation process. The fermentation can include the steps of providing at least one or more activators from Table 4 at any time during the course of the fermentation in a liquid culture at a level of at least 1 g/L, typically from about 1-50 g/L, or 2-20 g/L, or 5-10 g/L as a sole, or supplementary, carbon source to activate the cells.

In various embodiments, sialidase and/or fucosidase gene expression or enzyme assay activity are one means of confirming activation in a culture or a freeze-dried powder. Increased expression of solute binding proteins are also a functional consequence of activating the HMO pathway. (This increases *Bifidobacterium* binding to epithelial cells). Blon0042 is a transcriptional regulator gene for the HMO cluster and its functional analogs in other strains. Proteins that are at least 70% homologous to Blon0042 may be detected as an indicator of activation.

Low water activity is required to keep organisms dormant during long-term storage. In some embodiments, the stability of the activated *Bifidobacterium* or other bacteria in powder form requires water activity less than 0.35, less than 0.25, less than 0.2, less than 0.1. In other embodiments, anhydrous oils are used to maintain the organism in a stable dormant state in an oil suspension including, but not limited to, medium chain triglyceride (MCT), a natural food oil, an algal oil, a fungal oil, a fish oil, a mineral oil, a silicon oil, a phospholipid, and a glycolipid. Oils have low water activity, and edible oils, e.g. medium chain triglycerides, mineral oils, vegetable oils, can be blended with the *Bifidobacterium* comprising a functional H5 gene cluster, including the Deposited *Bifidobacterium*, whether activated or not. Syrups or other excipients with low enough water activity with or without others stabilizers may be used to keep cells dormant until use.

The composition can also include a food source that contains all the nutritional requirements to support life of a healthy mammal. That mammal may be, but is not limited to, an infant, an adolescent, an adult, or a geriatric adult. The food source can be a nutritional formulation designed for a human, buffalo, camel, cat, cow, dog, goat, guinea pigs, hamster, horse, llama, pig, rabbit, sheep, monkey, mouse, or rat. For example, the food source can be a food source for an infant human which further comprises a protein such as, but not limited to, a milk protein, a cereal protein, a seed protein, or a tuber protein. The food source can be mammalian milk including, but not limited to, milk from human, bovine, equine, caprine, or porcine sources. The food can also be a medical food or enteral food designed to meet the nutritional requirements for a mammal, for example, a human.

The composition may also comprise from about 5 to 90% of dietary glycans from a mammalian source including, but not limited to a human, swine, or bovine species.

The *Bifidobacterium longum* subsp. *infantis* comprising a functional H5 gene cluster, including the Deposited *Bifidobacterium*, whether activated or not, may be in single use or multiple use packaging in a vial, sachet, stickpack, capsule, tablet or other food product.

Compositions

The compositions described herein comprise a *Bifidobacterium longum* subsp. *infantis* comprising a functional H5 gene cluster, including the Deposited *Bifidobacterium*, such as EVC001 deposited under ATCC Accession No. PTA-125180, optionally with at least one complex oligosaccharide that contains a Type I or Type II core Lactose-N-biose moiety. The presence of this complex oligosaccharide may induce a change in the bacteria such that the complex oligosaccharide then becomes an energy source for the bacteria, and when the compostions is ingested by a mammal, the induced or activated bacteria provides a benefit to the gut of that mammal. Such compositions may be used for any of the methods described in International Patent Publications WO 2016/065324, WO 2016/149149, WO 2017/156548, WO 2017/156550, WO 2018/006080, and U.S. Provisional Application Nos. 62/558,344; 62/558,349; 62/613,405; and 62/618,293, where the methods call for *B. infantis* or similar microbes; where any of these methods also call for complex oligosaccharides, such as those found in MMO, the oligosaccharides preferably comprise one or more molecules having type 1 lacto-N-biose cores.

Suitable compositions comprise *B. infantis* and any galactose-N-acetyl galactosamine trimer, (eg., Gal-(1→3)-D-GlcNAc-(1→3)-Gal, or Gal-(1→3)-D-GlcNAc-(1→4)-Gal, or Gal-(1→6)-D-GlcNAc-(1→4)-Gal, or Gal-(1→6)-D-GlcNAc-(1→3)-Gal), and derivatives thereof.

Complex Oligosaccharide

In various embodiments, the composition comprises plurality of oligosaccharides. The oligosaccharide composition may be derived from human and non-human glycan sources and may exist as free glycans or protein-bound glycans. In some embodiments, the oligosaccharide can be a bovine or human milk oligosaccharide. In some embodiments, the oligosaccharide composition comprises bovine milk oligosaccharides (BMOs). Bovine oligosaccharides may comprise oligosaccharides from mature milk, early milk, colostrum, or concentrates thereof. In some embodiments, the oligosaccharides can include, but are not limited to, fucose, sialic acid, N-acetylglucosamine, and/or gluconate residues.

Compositions and Formulations of Oligosaccharides

Selective oligosaccharides (OS) as defined here are carbohydrates that are not digested by the mammal and are selective for particular bacteria. Selective oligosaccharides may be of mammalian milk, plant, algae, yeast origin provided they induce the desired metabolic profile. OS, as used herein, refers to those indigestible sugars of length DP2-DP20 from any source including plant, algae, yeast, or mammal. Oligosaccharides having the chemical structure of the indigestible oligosaccharides found in any mammalian milk are called OS herein, whether or not they are actually sourced from mammalian milk.

The OS can include one or more of lacto-N-biose, lacto-N-triose, lacto-N-neotetraose, fucosyllactose, lacto-N-fuco-pentose, lactodifucotetraose, sialyllactose, disialyllactone-N-tetraose, 2'-fucosyllactose, 3'-sialyllactosamine, 3'-fucosyllactose, 3'-sialyl-3-fucosyllactose, 3'-sialyllactose, 6'-sialyllactosamine, 6'-sialyllactose, difucosyllactose, lacto-N-fucosylpentose I, lacto-N-fucosylpentose II, lacto-N-fucosylpentose III, lacto-N-fucosylpentose V, sialyllacto-N-tetraose, or derivatives thereof. In some embodiments, the OS contains a Type I core. In a preferred embodiment of the mixture, the OS contains a type II core. See, e.g., U.S. Pat. Nos. 8,197,872, 8,425,930, and 9,200,091, the disclosures of which are incorporated herein by reference in their entirety. Functional equivalents of MMO may include identical molecules produced using recombinant DNA technology described in, for example, Australia Patent Application Publication No. 2012/257395, Australia Patent Application Publication No. 2012/232727, and International Patent Publication No. WO 2017/046711.

The OS composition (structures present) and their amount (grams) may support colonization and activation of *B. infantis*. The OS composition may maintain the activation of *B. infantis*.

The OS, including MMO and their functional equivalents such as, but not limited to, MMO separated from natural milks, synthetic nature-identical MMOs, modified plant polysaccharides, modified animal polysaccharides, or glycans released from animal or plant glycoproteins, support growth and metabolic activities of these bacteria and thus may be used in this invention.

The MMO may be provided to the mammal in the form of a food composition. The food composition can include mammalian milk, mammalian milk derived product, mammalian donor milk, an infant formula, milk replacer, or enteral nutrition product, or meal replacer for a mammal including a human. In some embodiments, the addition of the bacterial composition and the food composition that includes MMO can occur contemporaneously, e.g., within less than 2 hours of each other.

The MMO used for this invention can also include lacto-N-fucopentose (LNFP) and lactodifucotetraose (LDFT), lacto-N-tetraose (LNT) and lacto-N-neotetraose (LNnT), which can be purified from mammalian milk such as, but not limited to, human milk, bovine milk, goat milk, or horse milk, sheep milk or camel milk, or produced directly by chemical synthesis. LNnT has oligosaccharide structure that contains the Type II core. An example of a Type I core is LNT.

The MMO can also be sialyllactose (SL) or derivatives of SL such as, but not limited to, 3'sialyllactose (3SL), 6'sialyl-lactose (6SL), and disialyllacto-N-tetraose (DSLNT), which can be purified from mammalian milk such as, but not limited to, human milk, bovine milk, goat milk, or mare's milk, sheep milk or camel milk, or produced directly by chemical synthesis. The composition may additionally comprise one or more bacterial strains with the ability to grow and divide using sialyllactose or derivatives thereof as the sole carbon source. Such bacteria will express the HMO phenotype, but not necessarily the proteins of the H5 gene cluster. Such bacterial strains may be naturally occurring or genetically modified and selected to grow on the sialyllac-tose or its derivatives, if they did not naturally grow on those oligosaccharides.

The MMO can be a mixture fucosyllactose (FL) or derivatives of FL and sialyllactose (SL) or derivatives of SL which are naturally found in mammalian milk such as, but not limited to, human milk, bovine milk, goat milk, and horse milk. The FL and SL or derivatives thereof may be found in a ratio from about 1:10 to 10:1.

The composition may comprise at least 5%, 10%, 15%, 20%, 25%, 30%, 35%, 40%, 45%, 50%, 55%, 60%, 65%, 70%, 75%, 80%, 85%, 90%, or at least 95% of N-acetyl-D-lactosamine (dimer; Type II core typical in LNnT). For example, the composition may comprise about 5%-95%, 10%-80%, 50%-75%, or 20%-60% of N-acetyl-D-lactosamine (dimer; Type II core typical in LNnT). Additionally, the compositions may comprise at least 5%, 10%, 15%, 20%, 25%, 30%, 35%, 40%, 45%, 50%, 55%, 60%, 65%, 70%, 75%, 80%, 85%, 90%, or at least 95% of Type I core HMO (Gal-(1,3)-beta-GlcNAc), synthesized by enzymes bearing homology to beta-3-galactosyltransferase 1 (B3GALT1) found in the human genome. For example, the composition may comprise about 5%-95%, 10%-80%, 50%-75%, or 20%-60% of Type I core HMO (Gal-(1,3)-Beta-GlcNAc). An oligosaccharide not found in human milk, such as a dimer structure or other intermediate dimer, including biose—e.g., lacto-N-biose—found during the synthetic production of oligosaccharides, can be used. The compostions may comprise 5%, 10%, 15%, 20%, 25%, 30%, 35%, 40%, 45%, 50%, 55%, 60%, 65%, 70%, 75%, 80%, 85%, 90%, or 95% of lacto-N-triose I (Gal-(1,3)-beta-GlcNAc-(1,3)-Gal), or lacto-N-triose II (GlcNAc-(1,3)-Gal-(1,3)-beta-Glu) or lacto-N-neotriose (Gal-(1,4)-beta-GlcNAc-(1,3)-Gal). For example, the composition may comprise about 5%-95%, 10%-80%, 50%-75%, or 20% 60% of lacto-N-triose I (Gal-(1,3)-beta-GlcNAc-(1,3)-Gal), or lacto-N-triose II (GlcNAc-(1,3)-Gal-(1,3)-beta-Glu) or lacto-N-neotriose (Gal-(1,4)-beta-GlcNAc-(1,3)-Gal). The MMO may provide 0.2 grams to 40 gram per day. The composition may comprise at least 5%, 10%, 15%, 20%, 25%, 30%, 35%, 40%, 45%, 50%, 55%, 60%, 65%, 70%, 75%, 80%, 85%, 90%, or at least 95% of the total carbohydrate as Type I or Type II core oligosaccharides.

MMO or similar selective oligosaccharides used at percentages above 5%, 10%, 15%, 20%, 25%, 30%, 35%, 40%, 45%, 50%, 55%, 60%, 65%, 70%, 75%, 80%, 85%, 90%, 95% diluted in non-specific carbohydrates such as, but not limited to galactooligosaccharides (GOS), fructoologosaccharides (FOS), Xylosoligosaccharides (XOS) or combinations thereof in percentages below 95%, 90%, 85%, 80%, 75%, 70%, 65%, 60%, 55%, 50%, 45%. 40%, 35%, 30%, 25%, 20%, 15%, 10%, 5%. These combinations provide degrees of increasing selectivity where the higher the proportion of MMO or sources of selective oligosaccharide structures, the greater the selectivity for certain bacteria such as, but not limited to *B. longum* subsp. *infantis*.

Modifying the oligosaccharide structure to increase sialylation (Sialyllactosamine) or fucosylation can further increase their selectivity. The formulation may comprise type II core dimers of lactosamine, and fucosylated and/or sialidated oligosaccharides as the specific carbohydrate fraction, the remainder of which is made up with non-specific carbohydrates.

The OS may be provided to the mammal directly or in the form of a food composition. The composition may further comprise a food, and the food can comprise partial or the complete nutritional requirements to support life of a healthy mammal, where that mammal may be, but is not limited to, an infant or adult. The food composition can include mammalian milk, mammalian milk derived product, mammalian donor milk, an infant formula, milk replacer, an enteral nutrition product, or meal replacer for a mammal including a human. The OS may be in the form of a powder or liquid (water-based or oil-based).

In various embodiments, complex milk oligosaccharides include an oligosaccharide consisting of 3 Hex moieties, 4 HexNAc moieties and 1 fucose (Fuc) moiety; an oligosaccharide consisting of 4 Hex moieties, 4 HexNAc moieties, and 1 Fuc moiety; an oligosaccharide consisting of 3 Hex moieties, 5 HexNAc moieties, and 1 Fuc moiety; an oligosaccharide consisting of 5 Hex moieties, 4 HexNAc moieties, and 1 Fuc moiety; an oligosaccharide consisting of 4 Hex moieties, 5 HexNAc moieties, and 1 Fuc moiety; an oligosaccharide consisting of 3 Hex moieties, 6 HexNAc moieties, and 1 Fuc moiety; an oligosaccharide consisting of 3 Hexose (Hex) moieties and 6 N-acetyl hexosamine (HexNAc) moieties; an oligosaccharide consisting of 4 Hex moieties and 3 HexNAc moieties; an oligosaccharide consisting of 3 Hex moieties and 4 HexNAc moieties; an oligosaccharide consisting of 6 Hex moieties and 2 HexNAc moieties; an oligosaccharide consisting of 4 Hex moieties and 4 HexNAc moieties; an oligosaccharide consisting of 3 Hex moieties and 5 HexNAc moieties; an oligosaccharide consisting of 5 Hex moieties and 4 HexNAc moieties; an oligosaccharide consisting of 4 Hex moieties and 5 HexNAc moieties; and an oligosaccharide consisting of 3 Hex moieties and 6 HexNAc moieties. Exemplary oligosaccharides include Lacto-N-Tetraose, Lacto-N-Neotetraose, Lacto-N-Fucopentaose I, Lacto-N-Fucopentaose II, Lacto-N-Fucopentaose III, Lacto-N-Fucopentaose V, Lacto-N-Hexaose, Para-Lacto-N-Hexaose, Lacto-N-Neohexaose, Para-Lacto-N-Neohexaose, Monofucosyllacto-N-Hexaose II, Isomeric Fucosylated Lacto-N-Hexaose (1), Monofucosyllacto-N-Hexaose, Isomeric Fucosylated Lacto-N-Hexaose (3), Isomeric Fucosylated Lacto-N-Hexaose (2), Difucosyl-Para-Lacto-N-Neohexaose, Difucosyl-Para-Lacto-N-Hexaose, Difucosyllacto-N-Hexaose, Lacto-N-Neoocataose, Para-Lacto-N-Octanose, Iso-Lacto-N-Octaose, Lacto-N-Octaose, Monofucosyllacto-Nneoocataose, Monofucosyllacto-N-Ocataose, Difucosyllacto-N-Octaose I, Difucosyllacto-N-Octaose II, Difucosyllacto-N-Neoocataose II, Difucosyllacto-N-Neoocataose I, Lacto-N-Decaose, Trifucosyllacto-N-Neooctaose, Trifucosyllacto-N-Octaose and Trifucosyl-Iso-Lacto-N-Octaose.

In some embodiments, the oligosaccharide described herein comprises two or more monosaccharides (e.g., at least a disaccharide or trisaccharide), and can be a bovine or human milk glycan, or the equivalent thereof that is chemically synthesized. The complex oligosaccharide may be, but is not limited to, (3Hex,4HexNAc, 1Fuc), (1Gal, 1GlcNAc, 1 NeuAc), and/or (1Glu, 1 Gal, 1 NeuAc (3' or 6')). In some embodiments, the oligosaccharide selected will have at least one mannose residue.

In some embodiments, the oligosaccharide described herein comprises any of Hex(4); Hex(4) HexNAc(2); and Hex(3) HexNAc(1) NeuAc(1) at levels greater than 1%. In another embodiment, the at least one oligosaccharide comprise one of the following ratios of constituents: 1) a ratio of Hex(2) NeuAc(1):Hex(2) HexNAc(1) less than 5.0; 2) a ratio of Hex(2) HexNAc(1):Hex (3) HexNAc(1) of greater than 1.0; 3) a ratio of Hex(2) HexNAc(1):Hex (3) HexNAc (2) of greater than 2.0; 4) a ratio of Hex(3):Hex (3) HexNAc (1) NeuAc(1) of less than 100; and 5) a ratio of Hex(2) HexNAc(1):Hex (4) NeuAc(2) NeuGc(1) of greater than 10.

Complex mammalian milk oligosaccharides (MMO) can be isolated from any number of sources and using methods known to those of skill in the art. For example, HMOs can be obtained from human milk using methods known in the art. Human milk may be provided by the International Milk Bank (Sparks, NV, USA) or any such equivalent milk bank. Human milk may be pasteurized and then centrifugally defatted, separating it into cream (predominantly fat) and skim (defatted product). The defatted skim milk may then be filtered using membranes with a 5-10 kDa cut off to concentrate a protein fraction (predominantly whey) and the permeate, comprising the complex HMOs, dried by spray drying. The composition of this dried HMO fraction is about 50% lactose and about 30% HMO with the remainder of the mass primarily peptides and ash. The HMO fraction is predominantly fucosylated. BMOs can be isolated similarly, using any number of sources and methods known to those of skill in the art.

Colostrum oligosaccharides (COs) can be isolated from mammalian sources such as, but not limited to cows (BCO), humans (HCO), goats (CCO), or sheep (OCO) and used in the instant invention. Colostrum can be used as whole colostrum or processed to selectively enrich the CO fraction. Processing steps could include, but are not limited to, ultrafiltration, pasteurization, centrifugation, and precipitation. In general, the processes are selected to remove, inhibit or destroy enzymes that degrade the COs. In some embodiments, additional processing steps can be used to sterilize the product to eliminate any potential bacterial or viral contamination. Such steps include, but are not limited to, conventional pasteurization, ultrahigh temperature (UHT) processes, gamma irradiation, freezing and thawing, sonication, and microfluidic disruption. In other embodiments, the lactose content of the BCO may be reduced using processes know in the art such as, but not limited to, the treatment of the extract with enzymes to degrade lactose or through mechanical or biological means of selective removal of lactose. In yet other embodiments of the invention, the liquid CO mixtures are concentrated and/or dried by processes such as, but not limited to, spray drying, freeze drying, fluid bed drying, tunnel drying, and drum drying.

In various embodiments, the complex oligosaccharide comprises at least 5%, 10%, 15%, 20%, 25%, 30%, 35%, 40%, 45%, 50%, 55%, 60%, 65%, 70%, 75%, 80%, 85%, 90%, or at least 95% of the dry weight of the composition.

In alternate embodiments, the complex oligosaccharide further comprises synthetically produced oligosaccharides comprising fucosyllactose (SPF) and/or synthetically-produced sialyllactose (SPS) or derivatives thereof including, but not limited to, 2'-fucosyllactose, 3-fucosyllactose, difucosyllactose, lacto-N-fucosylpentaose I, lacto-N-fucosylpentaose II, lacto-N-fucosylpentaose III, lacto-N-fucosylpentaose V, 3'-sialyllactose, 6'-sialyllactose, 3'-sialyl-3-fucosyllactose, sialyllacto-N-tetraose, and 6'-sialyllactosamine. The synthetically produced oligosaccharides (SPO) may be derived using any of the number of sources and methods known to those of skill in the art. For example, SPF is produced using standard purification protocols as disclosed in the US Pub. No. 20130035481, the contents of which are incorporated herein by reference.

The synthetically-produced oligosaccharides (SPOs) can be added to the biologically produced mammalian milk oligosaccharide (MMO) and make up from at least 5% to at least 80% of the dry weight of the composition. In some embodiments, the composition comprises a mixture of MMO and SPF and/or SPS. In various embodiments, the SPO is 1%, 5%, 10%, 15%, 20%, 25%, 30%, 35%, 40%, 45%, 50%, 55%, 60%, 65%, 70%, 75%, 80%, 85%, or 90% of the dry weight of the composition. In some embodiments, the SPF is 1-50% of the dry weight of the composition. In other embodiments, the SPO is 5-30% of the dry weight of the composition. In other embodiments, the SPO is 10-20% of the dry weight of the composition. The MMO comprises at least 1%, 5%, 10%, 15%, 20%, 25%, 30%, 35%, 40%, 45%, 50%, 55%, 60%, 65%, 70%, 75%, 80%, 85%, 90%, or at least 95% of the dry weight of the composition. In some embodiments, the MMO comprises BCOs wherein the BCOs comprise at least 20% of the dry weight of the composition. In another preferred embodiment, the BCOs comprise at least 50% of the dry weight of the composition. In another preferred embodiment, the BCOs comprise at least 70% of the dry weight of the composition. In some embodiments, the mass ratio of MMO:SPO is from 20:1 to 1:10. In some embodiment, the ratio is from 10:1 to 1:2, and in another embodiment, the ratio is from 5:1 to 1:1. In some examples, the ratio is about 10:1, about 9:1, about 8:1, about 7:1, about 6:1, about 5:1, about 4:1, about 3:1, about 2:1, about 1:1, about 1:2 about 1:4, about 1:5, about 1:6 about 1:3, about 1:3, 10:2, about 9:2, about 8:2, about 7:2, about 6:2, about 5:2, about 4:2 or about 3:2.

*Bifidobacterium* with a Functional H5 Gene Cluster

In various embodiments, the Deposited *Bifidobacterium* comprise *Bifidobacterium longum* subsp. *infantis* EVC001 deposited under ATCC Accession No. PTA-125180 which may be activated or not. The activated *Bifidobacterium* (ABI) is defined herein as the state of the cells, as measured by the up-regulation or down-regulation of genes including but not limited to those coding for oligosaccharide binding proteins, transport proteins, and enzymes responsible for the degradation of the complex oligosaccharides, which provides significant benefits to a newborn infant. Such benefits include, but are not limited to, a higher binding affinity to the gut mucosa, higher colonization of the GI tract thereby preventing growth of other bacterial clades, a higher production of short chain fatty acids, higher consumption of complex oligosaccharides, and a greater stimulation of the immune response as measured by positive alterations of immune response markers, relative to the organism in a pre-activated state (Lewis, et al., 2015, *Microbiome,* 3:13; Huda, et al., 2014, *Pediatrics,* 134:2 e362-e372).

In various embodiments, the bifidobacteria encodes gene clusters containing ATP-binding cassette (ABC) transporters and glycosyl hydrolases involved in HMO utilization, typically including a gene coding for a fucosidase. In some embodiments, the bifidobacteria contains a gene coding for a complex oligosaccharide transporter. In some embodiments, the bifidobacteria contains a gene coding for a fucose transporter. In many embodiments, the genes encoding these components are upregulated or expressed. The genes may be constitutively upregulated or induced.

Certain biomarkers may be induced and/or repressed as markers to predict an activated state for *Bifidobacterium* species, whereby the bacteria are optimally primed for complex oligosaccharide consumption. Suitable biomarkers identified with *B. longum* subsp. *infantis* activation include upregulated genes and downregulated genes. Exemplary upregulated genes include Blon_0042 (regulatory protein); Blon_R0015 (tRNA); Blon_R0017 (tRNA); Blon_R0021 (tRNA); and Blon_R0022 (tRNA). Exemplary downregulated genes include Blon_0518 (hypothetical protein); Blon_0785 (membrane lipoprotein (possible transporter component)); Blon_2167 (hypothetical protein); and Blon_2168 (phage shock protein C). Previously, these genes were not known to be associated with an activated cell.

In some embodiments, the activated *Bifidobacterium longum* subsp. *infantis* comprising a functional H5 gene cluster, including the Deposited *Bifidobacterium*, comprises gene Blon_0042, wherein gene Blon_0042 has been upregulated. The activated bifidobacteria may comprise gene Blon_2168, wherein gene Blon_2168 has been downregulated. In one embodiment, the activated bifidobacteria comprises gene Blon_0042 and gene Blon_2168, wherein gene Blon_0042 has been upregulated and gene Blon_2168 has been downregulated. The skilled person can readily adapt quantitative proteomic methods to determine the expressed levels of the gene products (e.g., mRNA and protein) for these genes, to confirm activation.

*Bifidobacterium longum* subsp. *infantis* comprising a functional H5 gene cluster, including the Deposited *Bifidobacterium,* may be activated by being cultivated in a medium comprising at least one oligosaccharide among the complex oligosaccharides described above for a sufficient period of time to undergo induction and biosynthesis of at least one metabolic enzyme. The oligosaccharides are typically sourced from, or are identical to, those mammalian milk oligosaccharides (MMOs) including, but not limited to, those from human milk and bovine milk. In some embodiments, the oligosaccharide can be a bovine or human milk oligosaccharide. In another embodiment, the oligosaccharide is obtained from mammalian colostrum. In some embodiments, the oligosaccharide composition comprises bovine milk oligosaccharides (BMOs). Bovine oligosaccharides may comprise oligosaccharides from mature milk, early milk, colostrum, or concentrates thereof. In some embodiments, the oligosaccharides include fucose as component saccharide residues. In an alternative embodiment, the MMO is supplemented with synthetically produced and purified oligosaccharides comprising fucosylated and/or sialylated oligosaccharides. In some embodiments of the invention, the synthetically-produced fucosyllactose (SPF), sialyllactose (SPS) or derivatives thereof are used to activate bifidobacteria in a way that is more human-like than when activated by BMOs alone. In another embodiment, the composition is used to upregulate operons other than the HMO cluster.

Any of the compositions described herein may be prepared by cultivating a bifidobacteria in an axenic culture (e.g., a culture with genetic homogeneity), and if the culture comprises bovine milk glycans (e.g., concentrated from bovine colostrum), the *Bifidobacterium longum* subsp. *infantis* comprising a functional H5 gene cluster, including the Deposited *Bifidobacterium,* will become "activated." In various embodiments, any of the compositions described herein can be made by isolating bifidobacteria; purifying the bacteria; inoculating a fermenter with the purified strains of the bifidobacteria; and culturing the bifidobacteria in the presence of a primary carbon source, and optionally complex bovine or human oligosaccharides; and harvesting the cells. The formulation can include the steps of providing at least one complex oligosaccharide at any time during the course of the fermentation in a liquid culture at a level of from about 1-50 g/L, or 2-20 g/L, or 5-10 g/L as a sole, or supplementary, carbon source to activate the cells.

In a further embodiment, the composition can comprise a total count of viable bacteria from about 0.1 million to 500 billion colony forming units (cfu) per gram dry weight. In another embodiment, the total count of viable bacteria comprises 50 million to 5 Billion, or 5 Billion to 100 Billion cfu per gram dry weight. In another embodiment, the total count of viable bacteria comprises 10 Billion to 50 Billion cfu per gram dry. In some embodiments, the *Bifidobacterium*

*longum* subsp. *infantis* comprising a functional H5 gene cluster, including the Deposited *Bifidobacterium*, concentration is from 10 to 100 g dry weight per liter. The fermentation products can also be concentrated by filtration or centrifugation. The *Bifidobacterium longum* subsp. *infantis* comprising a functional H5 gene cluster, including the Deposited *Bifidobacterium*, (including activated *Bifidobacterium longum* subsp. *infantis* comprising a functional H5 gene cluster, including the Deposited *Bifidobacterium*) can be dried by controlled desiccation processes such as, but not limited to, freeze drying.

Formulating Compositions

The composition comprising MMO and *Bifidobacterium longum* subsp. *infantis* comprising a functional H5 gene cluster, including the Deposited *Bifidobacterium*, can be prepared by mixing the two components together. Optionally, one can combine the harvested and/or dried activated bifidobacteria cells with a powdered form of a complex bovine or human milk oligosaccharide. The harvested and/or dried activated bifidobacteria cells and the powdered form of the complex bovine or human milk oligosaccharide can be in a single dose packet, which can contain from about 0.1 1 million to about 100 billion cfu/gram of bacteria and, optionally, from about 0.5 g to about 5 g of complex oligosaccharide. The complex bovine oligosaccharide can be present in a powder composition wherein the blend ratio of activated bifidobacteria cells to complex oligosaccharide is 30 billion cfu per 1.5 g powder complex oligosaccharide.

Any of the compositions described herein can further comprise a secondary metabolite. The secondary metabolite can be a short chain fatty acid, such as acetate, lactate, or combinations thereof. The compositions described herein can further comprise a stabilizer, such as a flow agent. Flow agents may include starch, silicon dioxide, tricalcium phosphate, powdered cellulose, magnesium stearate, sodium bicarbonate, sodium ferrocyanide, potassium ferrocyanide, calcium ferrocyanide, bone phosphate, sodium silicate, calcium silicate, magnesium trisilicate, talcum powder, sodium aluminosilicate, potassium aluminum silicate, calcium aluminosilicate, bentonite, aluminum silicate, stearic acid, and polydimethylsiloxane. The stabilizer can be a milk protein or another suitable pharmaceutical grade or infant formula grade diluent (e.g., lactose). The milk protein can comprise a protein fraction of non-fat dry milk.

Any of the compositions described herein can further comprise surface carbohydrate binding protein (e.g., solute binding proteins). The surface carbohydrate binding proteins can allow a more effective binding and interaction with the gut mucosa by binding to cell surface glycosylation of the gut mucosa and or mucous layers. This binding of surface carbohydrate can then exclude the binding of pathogenic bacteria.

In various embodiments, any of the compositions described herein may be dried (e.g., by spray-drying or freeze-drying), and formulated into a unit dose medicament, such as a packet, sachet, orally disintegrating tablet, foodstuff, capsule, lozenge, effervescent tablet, etc. The unit dose medicament can be formed from a variety of materials including without limitation plastic, or paper. In some embodiments, the unit dose medicament comprises a moisture barrier and/or oxygen barrier layer. Alternatively, the composition may be provided in a form for anal delivery, such as a suppository or in an enema. Preferably, the composition is packaged in sachets made using a moisture and/or oxygen impermeable polymer.

In various embodiments, any of the compositions described herein may be provided in a dry powder formulation, a solution, a suspension, or in a tablet or capsule format with or without an enteric coating. The dry powder can be freeze-dried or spray dried. The freeze-dried compositions are preferably frozen in the presence of a suitable cryoprotectant. The cryoprotectant can be, for example, glucose, lactose, raffinose, sucrose, trehalose, adonitol, glycerol, mannitol, methanol, polyethylene glycol, propylene glycol, ribitol, alginate, bovine serum albumin, carnitine, citrate, cysteine, dextran, dimethyl sulphoxide, sodium glutamate, glycine betaine, glycogen, hypotaurine, peptone, polyvinyl pyrrolidone, taurine, or combinations thereof. The enteric coatings include, but are not limited to, fatty acids, waxes, shellac, plastics, plant fibers, methyl acrylate-methacrylic acid copolymers, cellulose acetate succinate, hydroxy propyl methyl cellulose phthalate, hydroxy propyl methyl cellulose acetate succinate, polyvinyl acetate phthalate (PVAP), methyl methacrylate-methacrylic acid copolymers, cellulose acetate trimellitate, sodium alginate, Zein, or combinations thereof.

In some embodiments, the microbe is mixed with a cryopreservative such as but not limited to trehalose or glycerol under anaerobic conditions and frozen by processes such as, but not limited to, rapid freezing (chilling with liquid nitrogen), or by a controlled temperature reduction in a cryopreservation freezing system. Once frozen, the microbes can be dehydrated under vacuum using a process that best maintains the integrity of the microbe cells. The microbe concentration in the dry powder can be from 1 Billion to 500 Billion cfu/g. In some embodiments, the dry powder can be from 5 Billion to 100 Billion cfu/g, and in a most preferred embodiment the dry powder can be from 10 Billion to 50 Billion cfu/g.

In some embodiments of the invention, the powdered microbe is resuspended in an edible oil such as, but not limited to triglyceride oils (e.g., vegetable oil, olive oil, and medium chain triglycerides), diglyceride oils, monoglyceride oil, and silicone oils.

In various embodiments, the oligosaccharide composition can be dissolved in a polar liquid such as, but not limited to, water, physiological saline, mammalian milk, or an infant formula, and provided in a liquid form to the infant while the bifidobacteria are provided separately as a powder or suspension in a carrier liquid which may include a solution comprising of the glycan.

In various embodiments, the microbes and the oligosaccharide composition may be provided combined or provided separately. In some embodiments, the microbe is combined with an oligosaccharide in a single dose packet containing from about 1 to about 100 billion cfu of microbe and from about 0.5 to about 5 g of an oligosaccharide.

Use of Compositions for Improvement of Mammalian Health

In various embodiments, the compositions described herein are delivered as a pre-activated and purified composition of *Bifidobacterium longum* subsp. *infantis* EVC001 deposited under ATCC Accession No. PTA-125180 to a subject in need thereof substantially contemporaneously with delivery of compounds to the mammalian intestine to make the intestinal environment a more favored niche to the aforementioned purified composition of bifidobacteria, where the compounds may comprise complex oligosaccharides described above, synthetically produced and purified oligosaccharides, and/or secondary metabolites produced as a result of intestinal fermentation.

In various embodiments, the use described herein comprises monitoring the subject's intestinal microbiome before, during and/or after administration of the composition described herein. A variety of monitoring techniques are known to one of ordinary skill in the art. For example, a routine sample of the subject's feces may be analyzed for microbes qualitatively and/or quantitatively by standard processes well known in the art (See, e.g., Le Pare et al. (2014) Food and Nutrition Sciences (5): 71-78).

In some embodiments, the compositions described herein are administered to a subject in need thereof in an amount and for a duration effective to establish the population of bifidobacteria at high levels in the gastrointestinal tract of the subject. In some embodiments, the compositions described herein can be administered to a subject in need thereof in an amount and for a duration effective to maintain the population of bifidobacteria at high levels in the gastrointestinal tract of the subject. In some embodiments, the composition is administered daily in an effective amount to maintain the bifidobacteria population in the gut of the subject at greater than at least 5%, 10%, 20%, 30%, 40%, 50%, 60%, 70%, 80%, or at least 90% of the total fecal microbiome of the mammal.

In some embodiments, the composition comprising activated *Bifidobacterium longum* subsp. *infantis* EVC001 deposited under ATCC Accession No. PTA-125180 is administered to a subject in need thereof. In other embodiments, the composition comprising complex oligosaccharides supplemented with synthetically produced and purified oligosaccharide is administered to a subject in need thereof. In another embodiment, the composition comprising both activated bifidobacteria and complex oligosaccharide is administered to a subject in need thereof. In another embodiment, the composition comprising bifidobacteria, and complex oligosaccharides supplemented with synthetically produced and purified oligosaccharide is administered to a subject in need thereof.

In various embodiments, the bifidobacteria are administered at a dose of from 1 billion to 100 billion cfu of bifidobacteria and from 1 to 20 g of complex oligosaccharides per day. In some embodiments, a dose is administered from 5 to 50 billion cfu/day. In another embodiment, a dose is administered from 5 to 100 billion cfu/day. In another embodiment, the dose is administered from 10 to 25 billion cfu/day. In various embodiments, the complex oligosaccharide is administered in a dose of from 0.5 g to 5.0 g/day. In some embodiments, the dose is administered in a dose from 1.0 g to 3.0 g/day.

Selective growth of *B. infantis* containing an H5 gene cluster may be promoted by contemporaneous consumption of LNB or any galactose-N-acetyl galactosamine dimer (eg., $\beta$-D-Gal-(1→3)-D-GlcNAc); or more preferably any galactose-N-acetyl galactosamine trimer, (eg., Gal-(1→3)-D-GlcNAc-(1→3)-Gal, or Gal-(1→3)-D-GlcNAc-(1→4)-Gal, or Gal-(1→6)-D-GlcNAc-(1→4)-Gal, or Gal-(1→6)-D-GlcNAc-(1→3)-Gal) and derivatives thereof.

The doses may be presented in multiple (e.g., two, three, four, five, six, or more) sub-doses administered at appropriate intervals throughout the day. Alternatively, they may be administered in the same composition, or constituent components may be administered sequentially. In some embodiments, the treatment is maintained for a period of at least 1-week, 2-weeks, 3-weeks, or at least 4-weeks. In other embodiments, the treatment is administered for a period of from at least 2-months, 4-months, 8-months, 10-months, or at least 12-months.

The subject in need thereof can be, for example, an infant from birth to about 36 months post-conception. In additional embodiments, the compositions described herein may be administered to a woman in at least the third trimester of pregnancy. The composition administered during pregnancy may include either the bifidobacteria, the oligosaccharide, or both. In additional embodiments, the composition described herein is administered a therapeutic amount to an infant born vaginally or via cesarean section. The compositions described herein are administered to the infant immediately after delivery and thereafter for at least the first month to six months of the life of the infant. The composition may be administered directly to the infant or mixed with a liquid including, but not limited to breast milk, infant formula or water. For infants who are not breast fed, the compositions described herein may alternatively be administered in an infant formula and such compositions may preferably comprise both activated *B. infantis* and a milk-derived oligosaccharide. For infants born via cesarean section, compositions comprising of activated bifidobacteria and/or complex oligosaccharides may be administered. For infants born vaginally, compositions comprising activated bifidobacteria and/or complex oligosaccharides may be administered.

The subject in need of an organism with an H5 cluster, may be an infant in the first 100 days of life, an infant 0-6 months, 6-12 months, 1-2 years, a toddler, a child up to 17 years of age or an adult or an older adult (+55). The subject may be a pregnant woman. The pregnant woman may be in the third or $4^{th}$ trimester. The subject may be in need of prevention or treatment of a disease or condition or correction of either inadequate or excess nutrition. The conditions may include colic, diaper rash, improved sleep. Diseases may include nectrotizing enterocolitis, diabetes either type I or 2, obesity, inflammatory bowel disease, atopy and allergic disease, celiac disease. The subject may be recovering from an infection or have Group B strep.

The use may involve establishment or maintenance of a sustainable and persistant population of *B. infantis* EVC001 using particular oligosaccharides as an important source of oligosaccharides reaching the large intestine. The sustained colonization may be used to prevent or treat any number of disease or conditions.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

The examples contained herein are offered by way of illustration and not by any way of limitation.

EXAMPLES

Example 1

A Fermentation to Produce Dried Activated *Bifidobacterium infantis*

A MRS fermentation media was made that contained NAG as 100% of the carbon source. This represented 2% of the total media composition (wt/vol). The MRS media also contained sources of nitrogen, minerals, reducing agents and was autoclaved prior to addition of a *B. infantis* inoculum. The fermentation was carried out under anaerobic conditions for 72 hours, until the fermentation reached the stationary phase. The cells were separated from the spent media and concentrated. A cryoprotectant was mixed with the cells to stabilize before freeze-drying. Once dried, the formulation was analyzed for fucosidase activity compared to a dried formulation that had been grown on glucose/lactose. The activated *B. infantis* release nitrophenol from a colorless aryl-substituted glycoside via fucosidases expressed by activated *B. infantis*. In comparison, the assay fails to demonstrate released nitrophenol (yellow color) when incubated with control cells of *B. infantis* grown on glucose/lactose. The colorimetric difference was confirmed using a spectrophotometer to measure absorbance @ 450 nm. In the activated state the Absorbance was greater than 0.5 nm, and in the unactivated state it was less than 0.1 nm.

Example 2

Determining Level of NAG Required for Activation of *B. infantis*

A series of fermentations were conducted where *B. infantis* was grown on various concentrations of NAG and glucose. MRS broth was prepared without a carbon source. The carbon source was added at 2% of the media or 20 g/L. The carbon source was varied according to Table 5. The cells were grown to the stationary phase and spun down. The supernatant was removed and the cells lysed. RNA was extracted. The cells were tested for increase in gene expression of Blon_0881 and Blon_2343 by qPCR relative to Blon_0393. The $2^{\wedge}\Delta\Delta Ct$ was greater than 1 confirming activation for 5, 10, 15 and 20 g/L of NAG.

TABLE 5

| NAG/Glucose Proportions | |
| --- | --- |
| NAG g/L | Glucose g/L |
| 20 | 0 |
| 15 | 5 |
| 10 | 10 |
| 5 | 15 |
| 0 | 20 |

Example 3

Activation and Drying of a *B. infantis* Biomass

Cells grown on MRS media with lactose (20 g/L) as the carbon source are grown for 24 hours and harvested before being re-suspended in a buffered media containing 50% glucose and 50% sialic acid, representing 1% of the total media composition (wt/vol) for 2 hours. The cells are tested for increase in gene expression of Blon_0881 and Blon_2343 by qPCR relative to Blon_0393.

Example 4

Preparation of an Activated Bifidobacteria (ABI) Composition that can Exclusively Use Certain Complex Oligosaccharides.

*Bifidobacteria longum* subsp. *infantis* (alternatively *B. infantis* herein) was isolated and purified from the feces of a vaginally delivered, breast fed human infant and its identification was confirmed by DNA analysis that reflected the presence of a gene set that is specifically associated with this organism (Sela et al., 2008, *PNAS*, 105(48): p. 18964-69). Alternatively, a strain of *B. infantis* can be obtained from a commercial culture collection such as the American Type Culture Collection (ATCC) of Washington, DC.

A seed culture of this organism was added to a growth medium comprising glucose and a BCO composition, made using the process described in Example 1, and other standard salts and vitamins in a 500 L agitated fermenter. Following 3 days of growth under anaerobic conditions, a sample of the culture was tested for the presence of activated *Bifidobacterium* (ABI). ABI was identified by the presence of gene transcripts for fucosidase or sialidase. The fermenter was harvested by centrifugation, and the concentrated cell mass was mixed with a cryopreservative (e.g., trehalose plus milk proteins) and freeze dried. The final dry product was 5.5 kg of bacterial mass with a count of $130\times10^9$ cfu/g. The activated *B. infantis* released nitrophenol from a colorless aryl-substituted glycoside via fucosidases. The cells were tested for increase in gene expression of Blon_0881 and Blon_2343 by qPCR relative to Blon_0393. The $2^{\wedge}\Delta\Delta Ct$ was greater than 1 confirming activation.

This example demonstrates that bifidobacteria can be activated by culturing the bifidobacteria with a complex bovine milk oligosaccharide. While BCO was used herein, this method or a similar method can be used to obtain ABI by culturing with MMO from any mammalian milk. Such ABI would be suitable for use in embodiments of this invention.

Example 5

Bifidobacteria Grown on Complex Oligosaccharides is Activated for Consumption of Milk Glycans.

*B. infantis* EVC001 was grown in MRS broth containing 2% lactose or bovine milk oligosaccharides (BMO). Cells were collected at exponential phase, RNA was purified and converted to cDNA and sequenced on an Illumina platform. Results clearly show differential expression during growth on BMO.

FIG. 1 depicts whole genome expression analysis. The diagram shows principle component analysis of all expressed genes within *B. infantis*. The diagram clearly shows differential expression of cells grown on BMO versus cells grown on lactose. 577 genes are differentially expressed suggesting growth on milk glycans induces a different physiological state in *B. infantis* than lactose.

Further analysis shows that the 40 kb milk glycan consumption gene cluster previously identified in *B. infantis* is preferentially induced during growth on BMO by comparison to growth on lactose. These results clearly show *B. infantis* grown on BMO is activated for consumption of milk glycans and a range of other genes involved in colonization and host interface in the neonate colon, including Blon_2334, Blon_2335, Blon_2336, Blon_2337, Blon_2338, Blon_2339, Blon_2344, Blon_2346, Blon_2347, and Blon_2331, are upregulated.

Example 6

Therapeutic Compositions for the Treatment of Pregnant Women.

Different preparations may be used to deliver desired compositions to pregnant women. Multiple dosage formats may be used for ease of use, sensory considerations and other reasons.

A first Preparation is made by first diluting the ABI product of Example 4 with lactose to provide a dose of 25 Billion cfu of *B. longum* subsp. *infantis* per gram. This diluted ABI product is then packaged in 2-piece gel caps (1 g/gel cap) made of a gastric-resistant polymer such as pectin, to provide doses of 25 Billion cfu of activated *B. longum* subsp. *infantis* per capsule in a delivery form that releases its contents in the GI tract beyond the stomach.

A second preparation uses maltodextrin in place of lactose to generate diluted ABI that is lactose-free for lactose intolerant individuals. This diluted ABI product is then packaged in 2-piece gel caps (1 g/gel cap) made of a gastric-resistant polymer such as pectin, to provide doses of 25 Billion cfu of activated *B. longum* subsp. *infantis* per capsule in a delivery form that releases its contents in the GI tract beyond the stomach.

A third preparation is made by blending the ABI product of Example 4 with a mixture of LNT and 2FL whereby 25 Billion cfu of *B. longum* subsp. *infantis* (170 mg of the dry product) is blended with 5 g of the LNT and 2FL powder. This preparation provides a ratio of 25 Billion cfu of *B. longum* subsp. *infantis* to about 2.5 g of oligosaccharide, and this mixture is packaged in sachets made using a moisture and oxygen impermeable polymer.

A fourth preparation packages single serving sachets of 5 grams LNnT powder into stickpacks A fifth preparation bulk packages spray-dried bovine colostrum enriched for oligosaccharides.

Example 7

Administering Composition to Pregnant Women

The compositions described herein are taken orally by a woman throughout pregnancy but at least in the third trimester of pregnancy.

A pregnant woman is provided with a treatment regime comprising two capsules/day of either the first or second preparation, as described in Example 6, in addition to 2 packages/day of the fourth preparation (LNT) for the first 2 weeks of treatment. This process establishes the population of *B. longum* subsp. *infantis* in the gut of the woman. Alternatively, the woman may be provided with 4 sachets per day of the 3rd preparation of Example 6 to maintain the population of *B. longum* subsp. *infantis* in her gastrointestinal tract. The 4 sachets are taken throughout the day, one at each meal and one before going to bed. The contents of the sachet can be mixed with milk, yogurt or pudding to aid in oral consumption. Compositions of this invention according to alternative embodiments may be administered similarly. Administration should be ideally initiated at the start of the 3rd trimester and continue until the birth of the child; it is expected to result in at least a 0.5-1 log change in *B. infantis* levels in the maternal stool. Once the *B. infantis* is established in the gut, the levels may be maintained by preparation 4 or preparation 5. In the case of a diagnosis of group B step, a high dose treatment protocol should be initiated to increase both the dose of *B. infantis* and LNT to 4 doses a day of each, but should also continue into the fourth trimester to at least 1 month post-partum. The treatment leads to a much higher likelihood that a vaginally-delivered infant will be appropriately inoculated with the *B. infantis* from the mother.

Example 8

Colonization of Breast-Fed Infants

Eighty mother-infant dyads were enrolled in either lactation support plus *B. infantis* supplementation (BiLS) or lactation support alone (LS). Starting with Day 7 postnatal, BiLS infants were fed $1.8$-$2.8 \times 10^{10}$ CFU *B. infantis* EVC001 deposited under ATCC Accession No. PTA-125180 daily in breast milk for 21 days. Mothers collected fecal samples, filled out health questionnaires, and kept daily logs about their infants' feeding and gastrointestinal symptoms from birth until Day 61 postnatal. Safety and tolerability were determined from maternal reports. The full study design is published in Smilowitz 2017 incorporated by reference herein [Smilowitz et al. BMC Pediatrics (2017) 17:133 DOI 10.1186/s12887-017-0886-9]

Study Population

This IMPRINT study was a parallel, partially-randomized, controlled 2-month trial. Prior to the initiation of the study, three separate randomization schemes were generated using a random number generator in Excel. Participants were stratified to one of the three randomization schemes based on mode of delivery—vaginal delivery, cesarean section (time of membrane rupture before delivery≤6 h), or cesarean section (time of membrane rupture before delivery>6 h). Parity and mode of delivery were not different between the two assigned groups for these fifteen participants.

After meeting major postpartum study criteria at enrollment (Day 3 or 4), infants were randomized into the BiLS or LS group. On Day 7, infants were screened for the consumption of infant formula within the past 24 h. On Days 3 or 4, 7, 15, 22, 33, and 61, study personnel visited mothers' homes to conduct study procedures. On all six visits, mothers filled out questionnaires about their and their infants' health, GI symptoms, occurrence of fever, illness, and number and reasons for sick doctor visits. Mothers collected infant stool samples from their infants' diapers before Day 6 (baseline) and on Days 10, 14, 21, 25, 29, 32, 40, 50, and 60 and stored them in their kitchen freezers. Infant weight was measured by study personnel with a digital infant scale (Tanita) on Days 33 and 61. Participants received breast-feeding support at their homes by the study's internationally board certified lactation consultant (IBCLC) prenatally and on Days 3 or 4, 7, and 15. On Days 22, 33, and 61 postnatal, study personnel transported samples from participants' homes to the UC Davis campus on dry ice and stored at −80° C.

Infants randomized into the BiLS group received one daily serving of *B. infantis* in their homes for 21 consecutive days starting on Day 7 and continuing through Day 27. During the Day 7 lactation consultation visit, mothers were trained by their lactation consultant to mix each *B. infantis* serving with 5 mL of their breast milk in a plastic medicine cup, and to syringe or finger-feed the mixture to their infants. Each daily serving of *B. infantis* EVC001 (ATCC Accession No. PTA-125180) consisted of one 625-mg sachet, delivering a minimum 156 mg of live bacteria (minimum $1.8 \times 10^{10}$ CFU) plus 469 mg of lactose as the excipient. The 18 billion CFU per sachet was the minimum guaranteed CFU count as determined by the product specification. All sachets were kept frozen in mothers' kitchen freezers until time of use, and mothers were instructed to keep all used and unused sachets provided. Compliance was assessed on Days 22 and 33 by counting and recording the number of empty *B. infantis* sachets.

Statistics

Data from the daily logs and retrospective questionnaires were binned into three time periods: baseline (Days 1-6), intervention (Days 7-27), and post-intervention (Days 28-61). For retrospective questionnaires, Day 7 data were binned as baseline. Means and proportions were calculated for continuous variables and categorical variables across all three time periods. Proportions for binary categorical variables were calculated as number of days reported/total number of days in each study period, and number of infants/total number of infants in each intervention group. The calculated values were multiplied by 100 to generate percentages.

For this Phase I study, the sample size was based on differences in infant fecal *B. infantis*, which was calculated using the means and standard deviations from a previous study on breastfed infants. Lewis et al. Microbiome 2015; 3(1): 13. To detect a standardized inter-group difference of 1.3 z-scores in infant fecal *B. infantis* with 90% power and $\alpha=0.05$, assuming equal standard deviations with a 20% attrition rate, 30 infants were needed in each group. Intent-to-treat analysis was performed of mother-infant dyads who initiated the study by Day 7 when final screening criteria were met. Statistical analyses were performed in IBM SPSS Statistics version 24 and figures were generated in PRISM v.7. Statistical significance was considered as p<0.05. Continuous data were checked visually for normality with histograms and quintile-quintile plots as well as numerically with the Shapiro-Wilk test and equality of variances using Levene's statistic. Non-normal data were $Log_{10}$ transformed and confirmed again for normality prior to conducting parametric analyses.

To determine differences in total infant fecal *Bifidobacterium* between groups, Mann-Whitney U test was conducted using GraphPad Prism v7. Baseline demographics, maternal health, pregnancy history, and infant feeding and GI symptoms were compared between the LS and BiLS groups using the Pearson Chi-square Test for Independence (categorical variables), Mann-Whitney U Test, or one-way ANOVA (continuous variables). For normally-distributed continuous data, repeated measures ANOVA was performed with group and time as fixed factors, parity as the covariate, and group by time as the interaction term. If time was significant, multiple comparison post-hoc analysis with Bonferroni correction was carried out to compare baseline, intervention, and post-intervention data. Group differences in stool consistency, flatulence, and spitting-up were analyzed by logistic regression.

Results

There were no differences in the mean gestational age at birth, weight 1 and 2 months postnatal, and breast milk intake between groups. The mean $Log_{10}$ change in fecal *Bifidobacterium* from Day 6 to Day 28 was higher (p=0.0002) for BiLS (6.6±2.8 SD) than for LS infants (3.5±3.5 SD). Daily stool number was higher (p<0.005) for LS and lower (p<0.05) for BiLS infants during supplementation than at Baseline. During supplementation, watery stools decreased and soft stools increased by 36% over baseline in BiLS infants (p<0.05) with no significant changes in stool consistency for the LS infants. None of the safety and tolerability endpoints, including flatulence, bloody stool, body temperature, ratings of gastrointestinal symptoms, use of antibiotics or gas-relieving medications, infant colic, jaundice, number of illnesses, sick doctor visits, or diagnoses of eczema were different for the groups at any point.

Study Participation

One-hundred and eight mothers were screened for eligibility to participate in the study. Eighty women met initial study criteria, of which fifteen were non-randomly assigned and sixty-five were randomly assigned into the LS (n=39) and BiLS (n=41) groups. Screen failures were due to the use of infant formula within 24 h of the Day 7 lactation consultation visit. Mothers withdrew from study participation for feeling overwhelmed with a new infant and/or unexpectedly discontinuing breastfeeding due to difficulty with lactation (n=8). Sixty-eight mother-infant dyads met final study criteria. Data for all participants in each group (n=34 per group) are reported except for the post-intervention period for the one participant who was enrolled into the LS group and withdrew on Day 26 postnatal.

Infant Characteristics

Infant birth weight, birth length, gestational age at birth, and gender were not different between groups. Infant weight was not different between groups at birth, or Days 33 and 61.

Infant Diet

According to maternal reports, the mean number of breastfeeds at the breast or with breast milk bottles by their infants was the same for intervention groups at each time period. The number of days, number of infants who were mixed-fed (consumed some amount of infant formula), or the mean amount of infant formula consumed were not significantly different between the BiLS and LS groups. One mother in the BiLS group and two mothers in the LS group reported feeding her infant non-study probiotics during the post-intervention period. The intake of vitamin D by infants was not different between the intervention groups (data not shown).

Infant Gastrointestinal Health and Tolerability

The number of infant bowel movements during the baseline period was the same for the BiLS and LS groups but was significantly (p<0.0005) different during the intervention (BiLS: mean, 3.2/d, range, 0.50-7.2; LS: mean, 5.5/d, range, 2.6-10.6), and post-intervention (BiLS: mean, 1.7/d, range, 0.30-4.8); LS: mean, 4.4/d, range, 0.97-9.9) periods The mean number of bowel movements was not only different between groups (p<0.01) but also different across time within each group (p<0.0005). Parity was unrelated to the reported mean number of bowel movements per day across all three time periods. Maternal reports for the proportion of watery and soft stools during the intervention period for infants in the BiLS vs. the LS group (0.20 vs. 0.33) and (0.79 vs. 0.67), respectively, were not statistically significant. Yet, the percentage of watery stools decreased from baseline to the intervention period by 36% in infants assigned to the BiLS group (p<0.05) and only by 7% in infants assigned to the LS group. As expected, the percentage of soft stools increased from baseline to the intervention period by 36% in infants assigned to the BiLS group (p<0.05) but only increased by 7% in infants assigned to the LS group. There was no difference in the change in consistency from intervention to post-intervention groups. Stool consistency was also not influenced by parity.

Infant illness and adverse events were not different between BiLS and LS groups (Table 7).

TABLE 7

| | | BiLS (n = 34) | | | | | | LS (n = 33) | | | | |
| | Baseline | | Intervention | | Post-Intervention | | Baseline | | Intervention | | Post-Intervention | |
| Tolerability Assessment | Mean | SD | Mean | SD | Mean | SD | Mean | SD | Mean | SD | Mean | SD |
|---|---|---|---|---|---|---|---|---|---|---|---|---|
| Temperature Above 100.3 F., % (# days)[a] | 0.005 | 0.029 | 0.000 | 0.000 | 0.000 | 0.000 | 0.005 | 0.029 | 0.000 | 0.000 | 0.001 | 0.005 |
| Blood in Stool, % (# days)[a] | 0.000 | 0.000 | 0.003 | 0.016 | 0.002 | 0.010 | 0.000 | 0.000 | 0.000 | 0.000 | 0.005 | 0.031 |
| Antibiotic Use, % (# days)[a] | 0.000 | 0.000 | 0.000 | 0.000 | 0.000 | 0.000 | 0.000 | 0.000 | 0.013 | 0.073 | 0.000 | 0.000 |
| Medication for Gas, % (# days)[a] | 0.015 | 0.086 | 0.038 | 0.088 | 0.084 | 0.194 | 0.005 | 0.029 | 0.059 | 0.167 | 0.142 | 0.254 |
| Jaundice diagnosis, % (n)[b] | 26.5% | (9) | 5.9% | (2) | 0% | (0) | 26.5% | (9) | 8.8% | (3) | 2.9% | (1) |
| Colic, Parental Report, % (n)[b] | 0% | (0) | 0% | (0) | 5.9% | (2) | 5.9% | (2) | 8.8% | (3) | 8.8% | (3) |
| Eczema diagnosis, % (n)[b] | 0% | (0) | 0% | (0) | 5.9% | (2) | 0% | (0) | 0% | (0) | 8.8% | (3) |
| Illnesses, % (# reports)[b] | 2.9% | (1) | 11.8% | (4) | 20.6% | (7) | 2.9% | (1) | 8.8% | (3) | 17.6% | (6) |
| Sick Doctor Visits, % (# reports)[b] | 2.9% | (1) | 15% | (5) | 15% | (5) | 0% | (0) | 2.9% | (1) | 12% | (4) |

[a]Proportions were calculated as: (number of days reported)/total number of days in each study period
[b]Percentages were calculated as: (number of infants for which condition appeared or was diagnosed)/total number of infants in each intervention group during each study period*100

Fecal *Bifidobacterium*

To correlate safety endpoints with the supplementation of *B. infantis* EVC001 and colonization of the genus *Bifidobacterium* in the infant gut, we compared the mean differences for total fecal *Bifidobacterium* from baseline to the end of the supplementation period for the LS and BiLS groups. The mean $Log_{10}$ change in total fecal *Bifidobacterium* from Day 6 to Day 28 was significantly (p=0.0002) higher for infants in the BiLS group (6.6±2.8 SD) compared with infants in the LS group (3.5±3.5 SD). The median $Log_{10}$ change from Day 6 to Day 28 for total fecal *Bifidobacterium* was median 0.0 for infants in the LS group and 7.5 for infants in the BiLS group (p=0.0002).

We found that *B. infantis* EVC001 was well-tolerated and safely consumed by healthy term infants for 21 consecutive days. All adverse events reported by mothers enrolled in the study were typical of infants this age and the incidences were not increased by the *B. infantis* feedings.

The infants in the BiLS group passed fewer daily stools than infants in the LS group. Additionally, infants in the BiLS group were reported to pass "soft" stools more often and "watery" stools less often compared with infants in the LS group. Adverse events occurred in both groups based on evaluation of the presence of colic, number of sick doctor visits, illnesses, eczema diagnoses by a primary care providers, and use of antibiotics or gas-relieving medications. The types of events, however, were normal for infants of this age, were not serious in nature, and the incidence of adverse events was not greater in the BiLS group than in the LS group. The adverse events were not deemed related to the study procedures or feeding of *B. infantis*.

Example 10

In Vivo Competitive Fitness of *B. infantis* Strains with and without Functional LNB-ABC Transporter Pathway
Evaluation of *B. infantis* Strain Fitness Genome sequencing of the type strain *Bifidobacterium longum* subps. *infantis* (*B. infantis*) ATCC 15697 strain revealed a number of loci dedicated to the import and consumption of HMO, including 20 homologous genes encoding extracellular solute binding proteins (SBPfamily 1) [Sela, et al. (2008). *Proc Natl Acad Sci USA* 105:18964].

The mode by which *B. infantis* captures and consumes HMO is unique amongst the bifidobacteria. *B infantis* selectively binds and imports HMO molecules through specific oligosaccharide binding F1SBP and ABC-type transporters. Once internalized, HMOs are hydrolyzed onto their monosaccharides components and metabolized via the "bifido shunt" pathway producing lactate and acetate as fermentation end-products Loss of integrity of gene F1SBPs and ABC transporters has been observed in in a subset of strains of *B. infantis* with limited ability to grow on pooled HMO [Lo-Cascio, et al (2010). *Appl Environ Microbiol* 76: 7373]. However, the functional and ecological implications of these strain-level differences have not been explored due to the lack of genetic knock out models for *Bifidobacterium*. The genomic diversity amongst *B. infantis* strains was assessed by performing global genome comparative analysis. The presence and distribution of key genes involved in importing HMO across strains of *B. infantis* was linked to growth phenotypes on HMO in vitro and the ability of strains to colonize and proliferate in vivo in the breastfed infant gut.

Materials and Methods

Bacterial strains used in this study (Table 8) were isolated from the stool of healthy breastfed infants, commercial probiotic products, and from the American Type Culture Collection (ATCC.org). Briefly, probiotic products or fecal samples were homogenized, diluted and cultured in selective media for bifidobacteria (BSIM). Plates were incubated at 37° C. in an anaerobic chamber maintained with a gas mix of 5% $H_2$, 5% $CO_2$, and 90% $N_2$ (Coy Laboratory Products) for 48-72 hours until distinguishable colonies were formed. Resulting colonies were streaked onto BSIM agar and after two passages they were grown in MRS broth supplemented with 0.05% l-cysteine-HCl. The identity of 10 randomly selected colonies per product was determined via Sanger sequencing of species-variable Internal Transcribed Spacer region within the rRNA locus, housed between the 16S and 23S rRNA genes using the forward 5'-CTKTTGG-GYYCCCKGRYYG-3' (SEQ ID NO: 1) and reverse 5'-CGCGTCCACTMTCCAGTTCTC-3' (SEQ ID NO: 2) primers. Confirmed *B. infantis* strains were stored at −80° C. in 15% glycerol. Prior to each assay all bacteria strains were struck on MRS plates and single colonies sub-cultured in MRS broth supplemented with 0.05% l-cysteine-HCl and incubated at 37° ° C. for 16 h in an anaerobic chamber.

genes across strains. Jaccard distances between presence/absence gene profiles were calculated to cluster strains based on pangenome profiles.

TABLE 8

General features of the bifidobacteria genomes included in this study

| Strain ID | isolation source | Size (kbp) | Coverage (x) | GC(%) | CDSs | tRNA's | Accession |
|---|---|---|---|---|---|---|---|
| ATCC 15697 | breastfed infant stool | 2832 | n/a | 59.8 | 2547 | 84 | |
| JCM 1222 | breastfed infant stool | 2828 | n/a | 59.8 | 2544 | 84 | GCA_000269965 |
| EVC001 | breastfed infant stool | 2832 | 147 | 59.8 | 2553 | 84 | |
| PI_001 | probiotic product | 2598 | 332 | 59.3 | 2226 | 59 | |
| PI_002 | probiotic product | 2604 | 185 | 59.3 | 2227 | 59 | |
| PI_003 | probiotic product | 2612 | 88 | 59.2 | 2232 | 59 | |
| PI_004 | probiotic product | 2604 | 172 | 59.3 | 2226 | 59 | |
| PI_005 | probiotic product | 2614 | 130 | 59.2 | 2233 | 59 | |
| PI_006 | probiotic product | 2615 | 171 | 59.2 | 2234 | 59 | |
| PI_007 | probiotic product | 2604 | 220 | 59.3 | 2228 | 59 | |
| PI_008 | probiotic product | 2612 | 213 | 59.2 | 2230 | 59 | |
| PI_009 | probiotic product | 2604 | 162 | 59.3 | 2230 | 59 | |
| PI_010 | probiotic product | 2609 | 117 | 59.2 | 2231 | 59 | |

DNA Extraction, Library Construction and Sequencing.

After 16 hours of growth, 3 mL cultures were centrifuged at 12,000×g for 2 min. High molecular weight (+30 Kb) DNA was extracted from the resulting cell pellets using the MasterPure Gram Positive DNA Purification Kit (Epicentre) following the manufacturer's instructions with an additional lysis step with achromopeptidase (5 U/μL) in conjunction with lysozyme. Extracted DNA was quantified using the Quant-iT™ dsDNA High Sensitivity Kit (Invitrogen) and checked for integrity in a 1% agarose gel.

Genome sequences were generated by a combination of paired end Illumina reads and MinION or PacBio long reads. Multiplexed short-read libraries were prepared using the Nextera XT Library preparation kit (Illumina) and sequences determined using a 2×300 paired-end Illumina MiSeq run with the University of California Davis DNA Technologies Core Facility. To generate Oxford Nanopore long reads, the Rapid Barcoding kit (SQK-RBK004) was used to prepare barcoded libraries according to the manufacturer's instructions. The sequencing library was loaded into the flow cell (R9.4.1). A 6-h sequencing protocol was selected on the MinKnow control software. PacBio sequencing was performed at the Vincent J. Coates Genomics Sequencing Laboratory at the University of California, Berkeley using a Pacific Biosciences RSII sequencer.

Hybrid Assembly of Bacterial Genomes, Annotation and Comparisons.

Bacterial genome assemblies were carried out using a hybrid assembly approach combining PacBio or MinION long reads with Illumina reads in Spades v3.11 [Bankevich, et al. (2012). J Comput Biol 19: 455] with parameters optimized for hybrid assemblies [Antipov et al. (2011). Bioinformatics 32: 1009] Assembled genomes were annotated with Prokka v1.12 [Seemann (2014). Bioinformatics 30: 2068] using default parameters. Bacterial genomes were visualized and globally compared using the BLAST Ring Image Generator (BRIG) v0.95 [Alikhan et al. (2011). BMC Genomics 12: 402]. A second comparison evaluating gene composition across strains was performed using a pangenome-based phylogenomic analysis with PanPhlan v1.2.3.2 [Scholz et al. (2016). Nat Methods 13: 435-438]. A pangenome database was created to track presence and absence of Growth on HMO Bacterial strains were tested for their ability to grow in Lacto-N-tetraose (LNT), Lacto-N-neotetraose (LNnT), 2' fucosyllactose (2'FL) and a combination of all three (mixedHMO, mHMO) as sole carbon source. Briefly, a 1% (v/v) standardized overnight cultures of each isolate were grown on modified MRS (mMRS) media containing (per liter), 2 g of ammonium citrate, 10 g of tryptone, 2 g of dipotassium phosphate, 0.2 g of magnesium sulfate, 0.05 g of manganese sulfate 0.5 g of L-cysteine HCL and 20 g of HMO. Growth profiles were monitored during 30 h by measuring optical density (OD600) using an Epoch2 spectrophotometer (Biotek) at 37° C. placed inside an anaerobic chamber maintained with a gas mix of 5% H2, 5% CO2, and N2 to balance (Coy Laboratory Products). Growth on pooled HMO (pHMO) was determined using RPMI 1640 media (Corning) under the same conditions described above. Three biological replicates were performed for each strain.

Glycoprofiling

Bacterial cultures in mMRS medium containing 20 g/L HMO were collected at 6 and 30 hours of growth representing mid lag phase and late stationary phase. Bacterial cells were removed by centrifugation at 10,000×g for 2 minutes. Supernatant was collected and diluted 10000-fold or 1000-fold for single and HMO mixtures, respectively. Dilutions were filtered through a 0.22 μm membrane and a 25 μL injection was analyzed on a High-Performance Anion-Exchange Chromatograph Coupled with Pulsed Amperometric Detection (HPAE-PAD ICS-5000, Thermo Scientific, Sunnyvale, CA) according methods from Lee et al. (2015). J Dairy Sci: 7644 with some modifications. Briefly, chromatographic separation was carried out on a CarboPac PA1 analytical column (4×250 mm, Dionex) and CarboPac PA1 guard column (4×50 mm, Dionex) with an isocratic gradient: 0-30 min 25% B, 1.5% C at 1.0 mL/min flow rate. Columns were equilibrated 8 min after each wash. Wash was done with 100% C. Solvent A was deionized water, solvent B 100 mM NaOH and solvent C was 500 mM NaOAc in 100 mM NaOH. HMO were quantified relative to a calibration curve ranging from 0.00025 to 0.005 mg/mL. All samples were analyzed in triplicate.

Strain-Specific Primer Development

A real-time PCR assay was developed to distinguish and quantify the presence of EVC001 and the PI_001 strain. The LNB phosphorylase gene ("Blon_2174" in strain ATCC 15697) was identified as a candidate region. Primer3 (Untergasser et al., 2012) Untergasser et al. (2012). Nucleic Acids Res 40: e115. was used to design the forward 2174_F and reverse 2147_R primers as well as the and strain-specific probes EVC001_probe and PI_001_probe. No unspecific amplification was detected. Additionally, when coupled with the probes, primers 2174_F and 2147_R did not produce false amplification from infants who were not previously fed B. infantis. Primer/probe efficiency was calculated for each primer/probe set using five 1:10 serial dilutions of the of genomic DNA extracted from a culture for which cell numbers had been determined.

Strain Competitions Tests

Competition assays between the PI_001 strain and EVC001 were tested over 30 h of co-coculture. Briefly, 16-hour cultures of each strain were standardized to an $OD_{600}$ of 1.0, combined at a 1:1 ratio and diluted 100-fold in 10 mL of MRS media containing 10 g/L of either LNT, LNnT, 2FL or mHMO. Total genomic DNA was extracted from bacterial cells from 1.0 mL samples collected at 6, 12 and 30 hours of anaerobic growth at 37° C. DNA extraction was performed using a KingFisher flex purification system (Thermo Scientific) with reagents from the ZymoBIOMICS 96 MagBead DNA kit (Zymo Research). Standard curves for all absolute quantification of each strain. were generated using genomic DNA extracted from previously quantified cultures of B. infantis EVC001 and B. infantis PI_001. Quantitative PCR was performed on a QuanStudio3 (Applied biosystems). The reaction mixture consisted of 0.5 μL of each primer (10 μM each), 5 μL of PerfeCTa Multiplex qPCR ToughMix, 11.5 μL of water and 5 μL of template DNA. The PCR conditions included 1 cycle of initial denaturation at 95° C. for 3 min, followed by 40 cycles of 95° C. for 15 sec and 60° C. for 1 min. Competitive index (CI) values were calculated as the ratio of the strains at a given timepoint normalized to the ratio of strains in the inoculum.

Relative Ecological Fitness Measurements

The relative fitness of the strains EVC001 and N1 in the ecological conditions of the breastfed infant gut was determined over a period of 3 days. The CFU of each strain in their respective commercial probiotic products was quantified by plating dilution series on BSIM agar plates were used to mix the strains at a 1:1 ratio. At day five of life, a vaginally born breastfed male infant was fed $8\times10^8$ of B. infantis ($4\times10^8$ of each strain) mixed with expressed breast milk. DNA was extracted from fecal samples collected one day prior and for three days after the infant was fed the strain combination. DNA extraction and strain quantification were performed as described for the strain competitive tests. Total B. infantis was quantified using methods by Lawley (Lawley et al., 2017).

Results

General Genome Features

In order to determine the gene content and genomic characteristics of the B. infantis strains, we sequenced and closed the genomes of 11 isolates obtained from probiotic products and performed a genome-wide comparative including publicly available genomes.

To facilitate a coherent comparative analysis, a uniform gene prediction analysis was performed for all sequenced B. infantis genomes and the genomes retrieved from public data bases. As outlined in Table 8. The number of predicted coding sequences ranged from 2227 for the B. infantis PI_002 to 2547 for the B. infantis ATCC 15697 strain. The percentage G+C content was calculated to be an average of 59.38±0.24%. The average genome size was 2659±97.9 Kbp with EVC001 having the largest genome (2832 Kbp) and PI_001 having the smallest (2598 Kbp). The genomes of ATCC and JCM 1222 and EVC001 were predicted to encode 84 tRNAs while the rest of the strains were predicted to encode 59 genes predicted as tRNA (Table 8).

Comparative Genomic Analyses

Figure 2A:
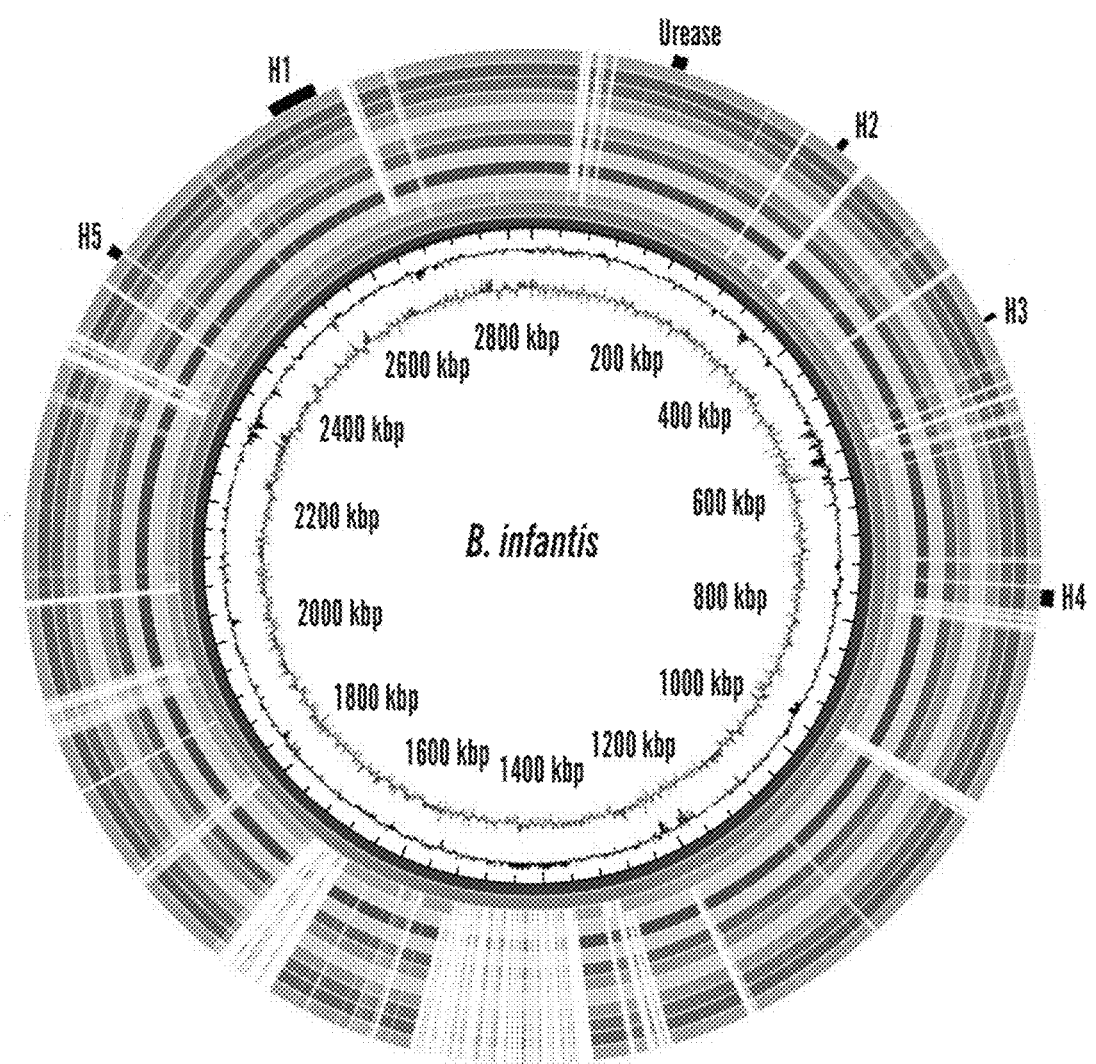
FIG. 2A. Circular map of twelve *B. infantis* strains in comparison to the type strain *B. infantis* ATCC 15697. The innermost rings represent the % G+C and the GC skew. HMO-utilization clusters are indicated in the outermost ring. The remaining circles display BLASTn searches against the genome of *B. infantis* ATCC 15697. Genomes circles are ordered sequentially as they appear in Table 1, beginning with the genome of ATCC 15697. Homology regions between 50% and 100% nucleotide identity are denoted from lightest to darkest shade, respectively. Regions with less than 50% identity appear as blank spaces in each ring.

To investigate the genetic content and genomic diversity of the B. infantis strains, the sequenced genomes of the probiotic-isolated strains were analyzed together with one publicly available genome (JCM 1222) and aligned using the type strain B. infantis ATCC 15697 as the reference genome. Two major chromosomal architectures were identified (FIG. 2A). The chromosomal backbones of the strains EVC001 and JCM 1222 were identical to the type strain. Conversely, alignment of the type strain with the rest of the strains was interrupted by various mobile genetic elements, including bacteriophage-related proteins, hypothetical proteins and transposases but also genes involved in the transport and metabolism of glycans.

To evaluate the degree of gene content variation between strains, we conducted a pangenome-based phylogenomic analysis using PanPhlan. This analysis revealed the presence of 3243 genes common among all 13 B. infantis genomes and 1639 that are present at least once in every examined genome, thereby representing the pan-genome and the core-genomes of the analyzed genome set. Intriguingly, not all genes predicted to HMO utilization were present in the core-genome set. Furthermore, this analysis also revealed the presence of 28 genes that are present in only one of the analyzed genomes. Eleven of unique genes were present in the genome of the strain EVC001. The type strain ATCC 15697 and the strain JCM 1222 were predicted to encode four unique genes each, PI_006 encoded five and PI_010 three and PI_009 one unique genes each. With a few exceptions the majority of the predicted strain-specific genes in the analyzed genome set were annotated as hypothetical proteins.

Figure 2B:
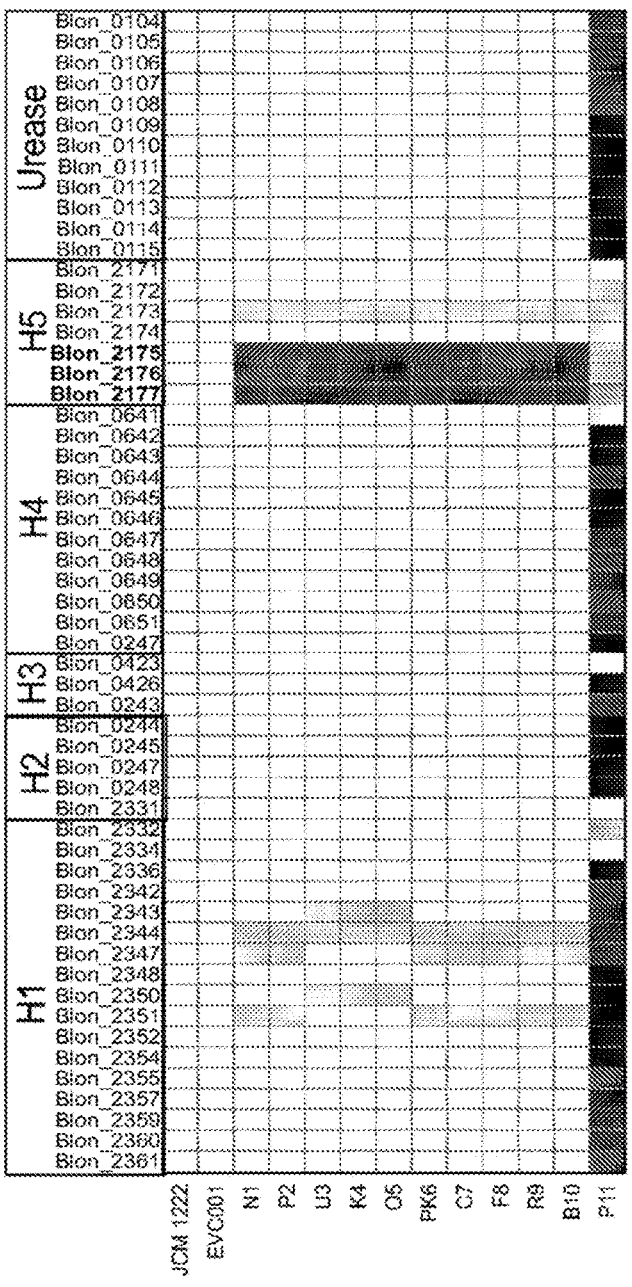
FIG. 2B. Heat map displaying the percent sequence identity (determined by TBLASTx) of HMO-utilization genes compared to the genome of *B. infantis* ATCC 15697. The shade of each tile of the heat map indicates the percent homology as indicated by the key.
Figure 2C:
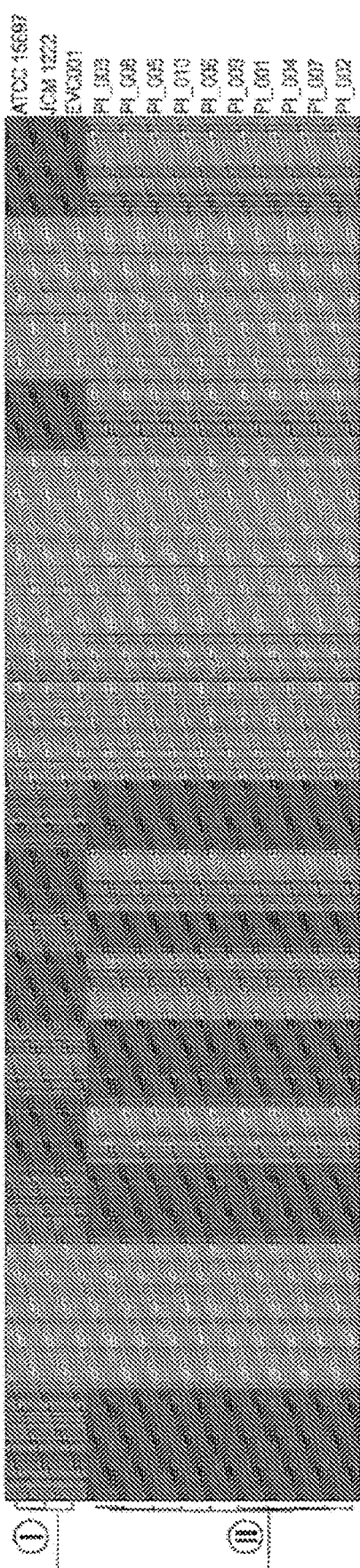
FIG. 2C. PanPhlan generated heatmap displaying presence/absence profiles of twelve *B. infantis* strains, including the type strain *B. infantis* ATCC 15697. Hierarchical clustering is induced by the presence/absence pattern of gene-families. Two distinct hierarchical clusters were generated and labeled 1 and 2.

Lastly, we conducted a hierarchical cluster analysis using a binary matrix of gene presence/absence the genes present in the pan-genome. According to this analysis, strains fall into one of two distinct clusters which correspond with the two genome architectures identified previously with whole genome alignments. Therefore, we classified strains in two groups. Strains with chromosomal architecture similar to the type strain in group I and strains dissimilar to the type strain, into group II (FIG. 2C).

Analysis of HMO-Utilization Genes

Figure 2D:
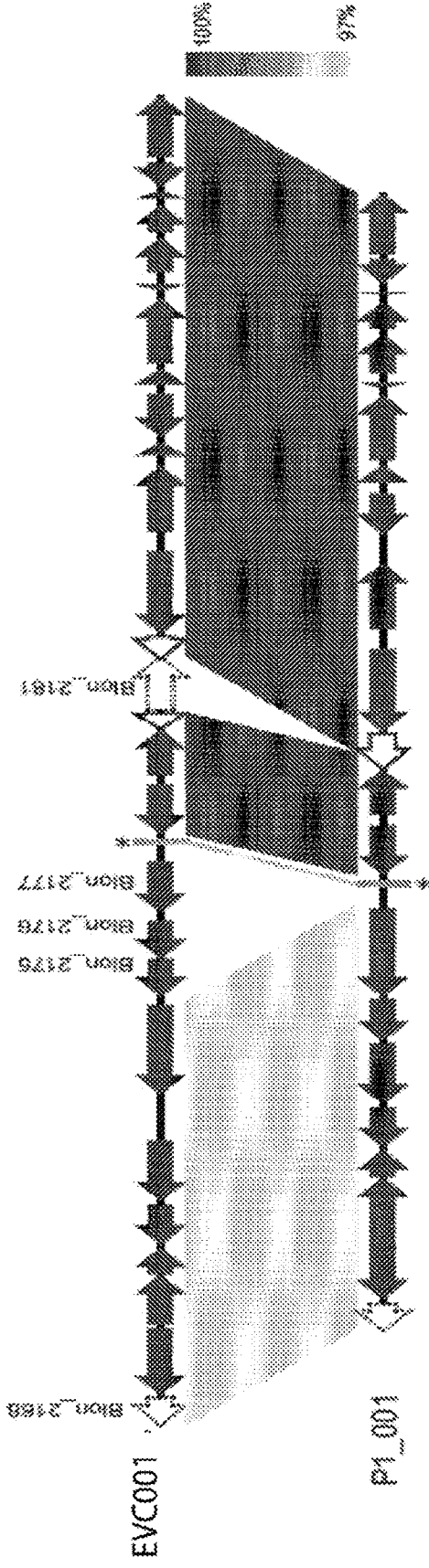
FIG. 2D. Alignment of a genomic containing the LNB metabolism gene cluster (H5). Genes belonging to the H5 cluster in type strain EVC001 are annotated with the corresponding Blon_locus tag. Homology at the nucleotide sequence level is indicated by greyscale blocks. Genes absent in the PI_001 strain are Blon_2175, Blon_2176 and Blon_2177. tRNAs are indicated with asterisks. Two genes related to mobile genetic elements, a phage shock protein (Blon_2168) and a transposon integrase (Blon_2181), are represented by arrows with dashed borders. Integration of Blon_2181 rendered a truncated anti-terminator gene in ATCC 15797, represented by the white arrows with a continuous border.

The genome of B. infantis ATCC 15697 encodes five gene clusters containing genes involved in HMO utilization. Gene sequences of the genes coded in all five HMO clusters were compared to the type strain B. infantis ATCC 15697 using TBLASTX. The H1 cluster encoding F1SBP, ABC-type transporters as well as fucosidases and sialidases was conserved in all B. infantis strains. However, divergence at the amino acid level<91% was identified in a few genes in subgroups of strains. Specifically, in the F1SBP Blon_2344 (all strains in group II), Blon_2347 and Blon_2351 (group II strains PI_001, PI_002, PI_003, PI_007, PI_008, PI_009, PI_010), Blon_2350 (group II strains PI_004, 005, 006) as well as the ABC transporter permease Blon2343 (group II strains PI_004, PI_005 and PI_0066) (FIG. 2B). The remaining HMO-clusters, H2, H3 H4 and the urease cluster were entirely conserved in all B infantis strains (FIG. 2B). The highest divergence occurred in the H5 cluster involved in the transport and metabolism of Lacto-N-Biose (FIG. 2B). In line with previous reports our analysis showed that the genes Blon_2175, Blon_2176 to Blon_2177 encoding an ABC-type transporter are absent in a subset of strains (FIG. 2B). Alignment of this regions in the ATCC 15697 and PI_001 strains revealed the presence of two genes related to mobile genetic elements located upstream and downstream of the ABC transporter genes, a phage shock protein (Blon_2168) and a transposon integrase (Blon_2181). Integration of Blon_2181 rendered a truncated anti-terminator gene in ATCC 15797 (FIG. 2D). The PI_001 genome encodes a gene homologous to Blon_2168 but not to Blon_2181 and possesses an intact anti-terminator gene (FIG. 2D). This indicates a chromosomal rearrangement event occurred following by an integration of a mobile genetic element, as it has been detected in other regions of the ATCC chromosome.

Growth on HMO

Figure 3A:
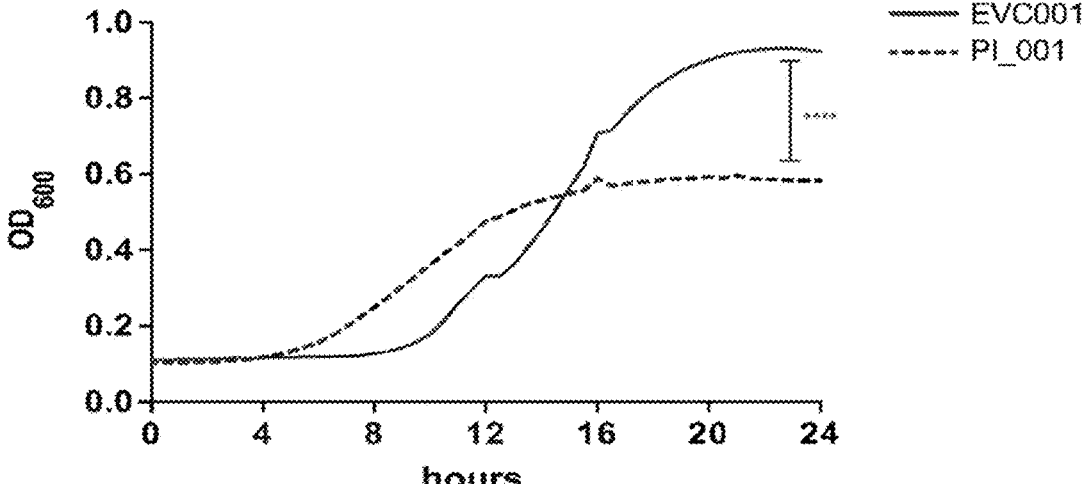
FIG. 3A. Growth curves of *B. infantis* EVC001 (group 1) and *B. infantis* PI_001 (group 2) strains in medium containing pooled HMOs.

The panel of *B. infantis* strains was assessed for growth on modified MRS (mMRS) supplemented with either 2% (wt/vol) LNT, LNnT, 2'FL or a combination of all three HMO at equal proportions (mixed-HMO), to represent the most abundant HMO in breast milk. Cell density was determined by $OD_{600}$ for 30 hours under anaerobic conditions at 37° C. Marked variation in the growth capacity of *B. infantis* strains in LNT, LNnT, and mixed HMO was observed between strains of group I and group II (Table 9). Strains from group I grew to high cell densities ($OD_{600}>1.2$) while strains in group II displayed moderate growth with the $OD_{600}$ values between $OD_{600}$ 0.5 and 0.9. Similar differences were found when the strains were grown on mixed-HMO, with strains in group I, reaching higher $OD_{600}$ values than strains in group II. Growth in 2'FL was moderate for all strains, with the $OD_{600}$ values never exceeding ($OD_{600}=0.9$). Select strains from groups I (strain EVC001) and group II (strain PI_001) were grown on pooled HMO from breast milk, as shown in FIG. 3A, the differences in growth were maintained with EVC001 reaching significantly higher densities (two-way ANOVA repeated measures, P<0.0001) than the PI_001 strain, beginning at 16 hours of growth (FIG. 3A). Strains were classified into high (HMO+), moderate (HMO±) or poor (HMO−) HMO-phenotype based on their growth profiles.

TABLE 9

Growth of *B. infantis* strains and a
*B. longum* strain on different HMO

| Stain | $OD_{600}$ at 30 h of growth[a] | | | | HMO phenotype |
| | LNT | LNNT | Mixed HMO | 2FL | |
| --- | --- | --- | --- | --- | --- |
| | Group I | | | | |
| EVC001 | + | + | + | ± | + |
| ATCC 15697 | + | + | + | ± | + |
| | Group II | | | | |
| PI_001 | ± | ± | ± | ± | ± |
| PI_010 | ± | ± | ± | ± | ± |
| PI_007 | ± | ± | ± | ± | ± |
| PI_003 | ± | ± | ± | ± | ± |
| PI_004 | ± | ± | ± | ± | ± |
| PI_005 | ± | ± | ± | ± | ± |
| PI_006 | ± | ± | ± | ± | ± |

TABLE 9-continued

Growth of *B. infantis* strains and a
*B. longum* strain on different HMO

| Stain | $OD_{600}$ at 30 h of growth[a] | | | | HMO phenotype |
| | LNT | LNNT | Mixed HMO | 2FL | |
| --- | --- | --- | --- | --- | --- |
| PI_002 | ± | ± | ± | ± | ± |
| PI_009 | ± | ± | ± | ± | ± |
| PI_008 | ± | ± | ± | ± | ± |

[a]Level of growth was classified as follows:
+, high ($OD_{600} > 1.0$);
±, moderate ($OD_{600} = 1$ to 0.4);
−, poor ($OD_{600} < 0.4$)

Glycoprofiling of HMO Consumption

Figure 3B:
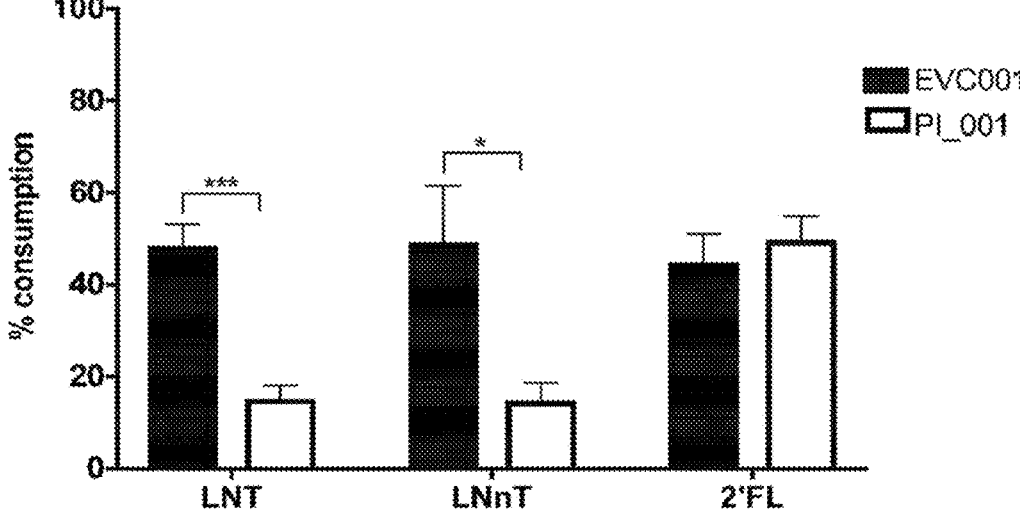
FIG. 3B. Glycoprofiles of bacterial supernatants after 30 h of cultivation. Consumption is calculated as the percent difference in HMO between the 6 h and the 30-hour timepoints.

To determine HMO consumption, the glycoprofiles of the spent media after 30 hours of HMO fermentation were determined on representative strains of groups I and II. As expected, based on growth results, consumption of LNT and LNnT, but not 2'FL was markedly different between the EVC001 (group I) and the PI_001 (group II) strain (FIG. 3B). The strain EVC001 consumed 48.4±4.7% of LNT HMO while the PI_001 strain consumed only 15.2±2.9% (Student's t-test, P=0.0005). Similarly, consumption of LNnT was significantly different (Student's t-test, P=0.0101) with the strain EVC001 consuming 49.1±12.4% and the PI_001 strain consuming 14.6±4.11%. Consumption of 2'FL was not significantly different (Student's t-test, P=0.3536) between strains, EVC001 consumed 44.7±6.43% and the PI 001 strain 49.7±5.23% (FIG. 3B). Trace amounts of NAG (0.34±0.11 mg/mL) were detected in the spent media of PI_001 but not of EVC001 grown on LNT, suggesting inefficient or partial hydrolysis of this substrate by the PI_001 strain.

Competitive Index

Figure 3C:
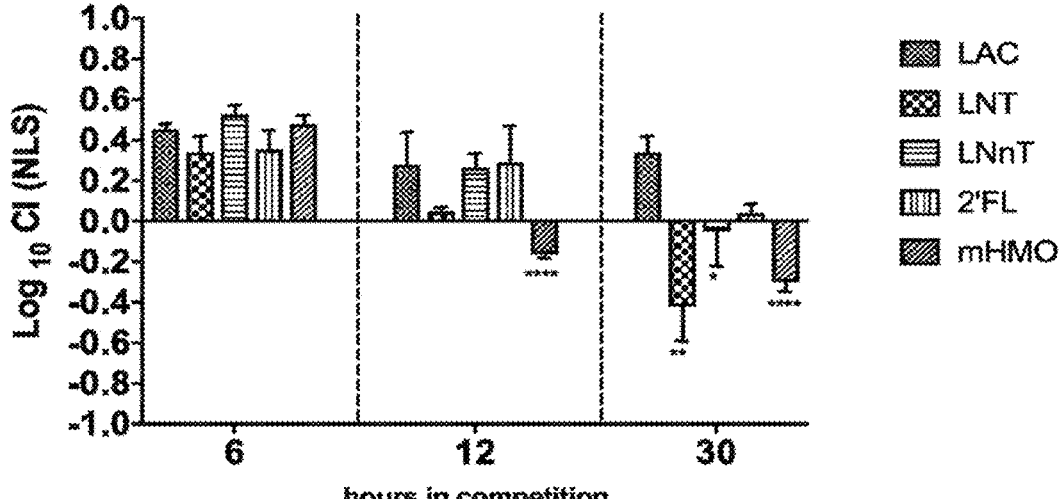
FIG. 3C. Competitive index (CI) analysis between the strains *B. infantis* EVC001 (group 1) and the *B. infantis* PI_001. Negative CI values indicate a decreased capacity of the PI_001 to compete for growth. Statistically significant differences in CI values between timepoints are indicated with asterisks (*P<0.05, P<0.01, *P<0.001).
Figure 4A:
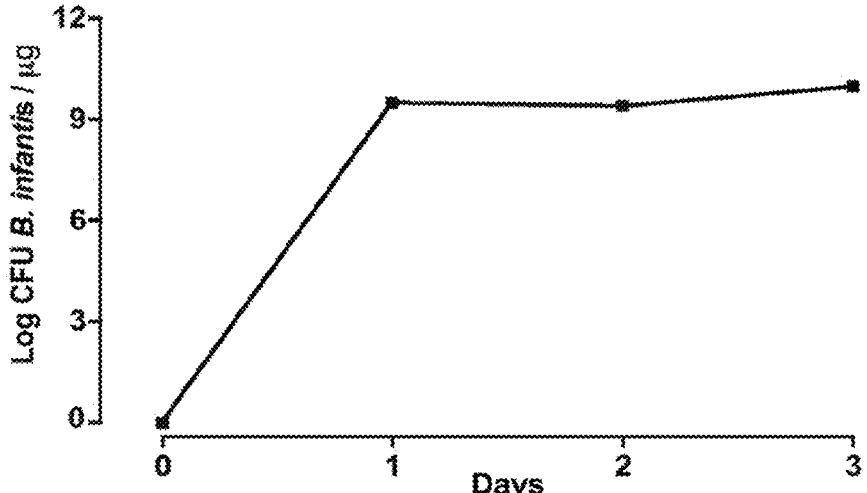
FIG. 4A. qPCR data showing the absolute levels of *B. infantis* before (day zero) and three days after feeding $4 \times 10^9$ of each strain *B. infantis* EVC001 and *B. infantis* PI_001 at a ratio of 1:1.
Figure 4B:
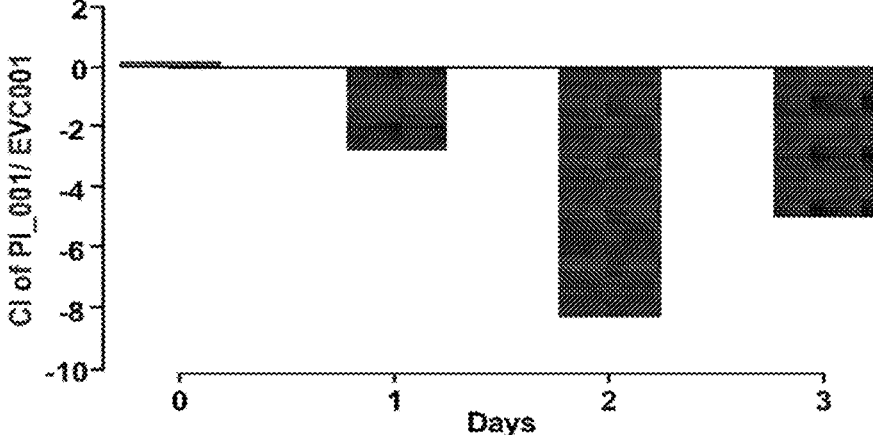
FIG. 4B. qPCR data showing the absolute levels of *B. infantis* before (day zero) and three days after feeding $4 \times 10^9$ of each strain *B. infantis* EVC001 and *B. infantis* PI_001 at a ratio of 1:1.

A competitive co-inoculation model was used to investigate the contribution of the Blon_2174-2177 genes to the ability of strains to grow on different HMO. As shown in FIG. 3C, at 12 h post-inoculation, the competitive index of the PI_001 strain on mixed-HMO was significantly attenuated (P=0.0001, One-way ANOVA, followed by Dunnett's test) when compared to that at 6 hours. By 30 hours, and as indicated by the CI negative values, the strain PI_001 had a significantly decreased its capacity to compete with EVC001 during growth on LNT (P=0.0056), LNnT (P=0.0210), and mixed HMO (P=0.0001), but not 2'FL (P=0.2026) or lactose (P=0.5105) (FIG. 4B).

To determine if the reduced competitiveness of PI_001 observed in vitro affected the ability of the strain to colonize the infant gut, we fed EVC001 and PI_001 to breasted infant at a 1:1 ratio and determine the competitiveness of PI_001 over a 3-day period. As shown in FIG. 4A, total *B. infantis* reached $10^9$ CFU/μg of fecal DNA by day one post-feeding, which is consistent with previous results observed after feeding EVC001 to breastfed infants (Frese et al., 2017). Next, using a stain-specific qPCR we determined the CFU/μg of fecal DNA of each strain and calculated the CI of the PI_001 compared to EVC001 over a 3-day period. As shown in FIG. 4B, and as indicated by the negative CI values, the strain PI_001 fails to compete with EVC001 in the gut of a breastfed infant starting at day one after both strains were fed to in the same numbers. Together, these results indicated that the ability to utilize LNT and LNnT is central to a strain's capacity to colonize the breastfed infant gut.

The lack of genetic tools to generate gene knockouts in *B. infantis* have hindered the experimental validation of the importance of different genes in *B. infantis* that explain the tripartite coevolutionary relationship between the mother's milk, the infant, and *B. infantis*. Group II represent a functional knock-out that advances the understanding of important features for better suitability to the infant gut.

This functional-genomic approach provided mechanistic understanding of metabolism of HMO in *B. infantis* strains. Analysis of the intraspecific genomic diversity of twelve *B. infantis* strains isolated from either breastfed infant feces and commercial probiotic products revealed the genetic variability among strains consisted mainly of hypothetical genes and mobile genetic elements, but also included genes predicted to be involved in the uptake of HMO. Specifically, in the Blon_2175-2177 ABC transport system located in the H-5 cluster. We demonstrate that there are 2 lineages of *B. infantis* strains: Group I and II strains. Group II, strains are impaired for growth in both LNT or LNnT as well as pooled HMO (Table 8, FIG. 4). The inability to access these glycans has an associated fitness penalty when it comes to colonization of the breasted infant gut, which supports the notion that the composition of human milk and *B. infantis* have coevolved to their mutual advantage.

The genomes of strains in group I encode numerous mobile genetic elements, suggesting their genomes have been shaped by the acquisition of novel genetic material Sela, et al. (2008). *Proc Natl Acad Sci USA* 105:18964.

consumption of HMO and in the colonization of the breast-fed infant gut. We found that the HMO consumption behavior of *B. infantis* is consistent with the metabolic ability deduced by the genomic analyses. The absence of this particular ABC transport system corresponded with impaired growth on LNT, LNnT and pooled HMO. LNT, LNnT and small (DP<7) type 1 and type 2 glycans are the most abundant HMO in breast milk, comprising up to 70% of the pool of HMO (LoCascio et al., 2007). Our results clearly show the role of the Blon_2175-2177 ABC transport system in mediating the metabolism of LNT and LNnT. The information gained from the in vivo characterization of these genes contributed to our understanding of the roles ABC transporter genes have in colonization of the *B. infantis* in the breastfed infant gut.

Based on results presented here, the success of a probiotic in colonizing the infant gut is very likely to be strain-specific. Therefore, careful considerations must be paid to genotypic and phenotypic characteristics necessary to be competitive in the be ecological conditions of the breastfed infant when selecting strains for probiotic applications.

The *Bifidobacterium longum* subsp. *infantis* comprising a functional H5 gene cluster, including the Deposited *Bifidobacterium*, appeared to show a competitive advantage over *B. infantis* not comprising a functional H5 gene cluster in colonization of a human gut in this study.

---

SEQUENCE LISTING

```
Sequence total quantity: 2
SEQ ID NO: 1            moltype = DNA  length = 19
FEATURE                 Location/Qualifiers
source                  1..19
                        mol_type = other DNA
                        organism = synthetic construct
SEQUENCE: 1
ctkttgggyy ccckgryyg                                             19

SEQ ID NO: 2            moltype = DNA  length = 21
FEATURE                 Location/Qualifiers
source                  1..21
                        mol_type = other DNA
                        organism = synthetic construct
SEQUENCE: 2
cgcgtccact mtccagttct c                                          21
```

---

(FIGS. 2A and C). The presence of various phage-related sequences in the neighboring regions to the Blon_2175-2177 indicate that horizontal transfer events shaped this region. However, the absence of intact prophage genes suggests that the integration did not occur recently. It remains unknown how a lineage of *B. infantis* strains lacking the Blon_2175-2177 ABC transporter emerged. Although, our work is in strains isolated from probiotics, which are known to be prone to phage infection and genome decay during production (Douglas and Klaenhammer, 2010) others have found similar genotypes in strains isolated from infant feces (LoCascio et al., 2010). It is nevertheless possible for these strains to have originated from an ingested probiotic product, as our own efforts to isolate *B. infantis* strains from control infants (not fed a *B. infantis* probiotic) from a previous clinical study (Frese et al., 2017) were unsuccessful. This would suggest that the absence of the Blon_2175-2177 ABC transporter is an artifact of a lineage of probiotic strains, likely acquired from a common stock and distributed by various manufacturers.

Results presented in this study provide a mechanistic assessment of the role of this ABC transport system in the

What is claimed is:

1. A composition comprising a *Bifidobacterium longum* subsp. *infantis* comprising a functional H5 gene cluster; wherein the *Bifidobacterium longum* subsp. *infantis* is *Bifidobacterium longum* subsp. *infantis* deposited under ATCC Accession No. PTA-125180; and wherein the composition is in the form of a dry powder, or a dry powder suspended in an oil; and/or wherein the composition further comprises a cryoprotectant; and/or wherein the composition further comprises a stabilizer.

2. The composition of claim 1, wherein the H5 cluster comprises Blon_2175, Blon_2176, and Blon_2177;

wherein the functional H5 cluster comprises Blon_2171, Blon_2173, Blon_2174, Blon_2175, Blon_2176, Blon_2177, and galT;

wherein the *Bifidobacterium* comprises upregulated genes selected from the group consisting of Blon_0042, Blon_R0015, Blon_R0017, Blon_R0021, Blon_R0022, and combinations thereof;

wherein the *Bifidobacterium* comprises downregulated genes selected from the group consisting of Blon_0518, Blon_0785, Blon_2167, Blon_2168 and combinations thereof;

wherein the *Bifidobacterium* comprises an upregulated Blon_0042 gene;

wherein the *Bifidobacterium* comprises a downregulated Blon_2168 gene;

wherein the *Bifidobacterium* comprises upregulated genes selected from the group consisting of Blon_0879, Blon_0880, Blon_0881, Blon_0882, Blon_2177, Blon_2334, Blon_2335, Blon_2336, Blon_2337, Blon_2338, Blon_2339, Blon_2343, Blon_2344, Blon 2346, Blon 2347, and Blon_2331;

wherein the *Bifidobacterium* expresses a gene coding for a sialidase or a fucosidase; and/or wherein the *Bifidobacterium* expresses a gene coding for a sialic acid or a fucose transporter.

3. The composition of claim 1, wherein the *Bifidobacterium* is activated by an activator, wherein the activator is selected from the group consisting of N-acetyl-glucosamine/galactosamine (NAG), Dimeric N-acetylglucosamine, Fucose, Sialic Acid, Lacto-N-biose (LNB), Galacto-N-biose and Fuc α1,2Galβ;

wherein the *Bifidobacterium* has been cultured in the presence of at least one mammalian milk oligosaccharide; and/or wherein the composition further comprises an activator selected from the group consisting of N-acetyl-glucosamine/galactosamine (NAG), Dimeric N-acetylglucosamine, Fucose, Sialic Acid, Lacto-N-biose (LNB), Galacto-N-biose and Fuc α1,2Galβ.

4. The composition of claim 1, wherein the *Bifidobacterium* contains a LNB transport system capable of internalizing one or more oligosaccharide having a Type I or Type II core before the oligosaccharide is hydrolyzed and is capable of hydrolyzing the internalized oligosaccharide, wherein the oligosaccharide is obtained from mammalian milk selected from human, bovine, pig, rabbit, goat, sheep, camel milk, or mixtures thereof.

5. The composition of claim 1, wherein the *Bifidobacterium* has a higher binding affinity to mammalian mucosal cells than Bifidobacteria of the same species cultivated in the absence of complex oligosaccharides.

6. The composition of claim 1, wherein the *Bifidobacterium* is present at a concentration of from 1 Million cfu/g to 500 Billion cfu/g;

wherein the *Bifidobacterium* is present at a concentration of from 5 Billion cfu/g to 100 Billion cfu/g; or wherein the *Bifidobacterium* is present at a concentration of from 10 Billion cfu/g to 50 Billion cfu/g or from 50 million cfu/g to 5 billion cfu/g.

7. The composition of claim 1, further comprising an isolated complex oligosaccharide.

8. The composition of claim 7, wherein the complex oligosaccharide is a mammalian milk oligosaccharide (MMO);

wherein the complex oligosaccharide is isolated from a mammalian milk source selected from human, bovine, pigs, rabbits, goats, sheep, or camel;

wherein the mammalian milk oligosaccharide (MMO) comprises oligosaccharide molecules found in human milk oligosaccharides (HMO), bovine milk oligosaccharides (BMO), bovine colostrum oligosaccharides (BCO), goat milk oligosaccharides (GMO), or a combination thereof;

wherein the bovine source is from bovine milk, bovine colostrum, bovine colostrum concentrate, or mixtures thereof;

wherein the bovine colostrum oligosaccharide comprises any of Hex(4); Hex(4) HexNAc(2); or Hex(3) HexNAc (1) NeuAc(1) at levels greater than 1%;

wherein the complex oligosaccharide is from whey permeate;

wherein the mammalian milk oligosaccharide (MMO) comprises lacto-N-biose, lacto-N-triose, N-acetyllactosamime, lacto-N-neotriose, lacto-N-tetraose, lacto-N-neotetraose, fucosyllactose, lacto-N-fucopentose, lactodifucotetraose, sialyllactose, disialyllactone-N-tetraose, 2'-fucosyllactose, 3'-sialyllactoseamin, 3'-fucosyllactose, 3'-sialyl-3-fucosyllactose, 3'-sialyllactose, 6'-sialyllactosamine, 6'-sialyllactose, difucosyllactose, lacto-N-fucosylpentose I, lacto-N-fucosylpentose II, lacto-N-fucosylpentose III, lacto-N-fucosylpentose V, sialyllacto-N-tetraose, their derivatives, or combinations thereof;

wherein the mammalian milk oligosaccharide (MMO) comprises lacto-N-biose; and/or wherein the mammalian milk oligosaccharide (MMO) comprises lacto-N-triose.

9. The composition of claim 7, wherein the complex oligosaccharide comprises at least one of (3Hex,4HexNac, 1Fuc), (1Gal, 1GlcNAc,1NeuAc), or (1Glu, 1Gal, 1NeuAc (3' or 6'));

wherein the complex oligosaccharide is less than 50% fucosylated;

wherein the complex oligosaccharide comprise one of the following ratios of constituents: 1) a ratio of Hex(2) NeuAc(1): Hex(2) HexNAc(1) less than 5.0; 2) a ratio of Hex(2) HexNAc(1): Hex (3) HexNAc(1) of greater than 1.0; 3) a ratio of Hex(2) HexNAc(1):

Hex (3) HexNAc(2) of greater than 2.0; 4) a ratio of Hex(3): Hex (3) HexNAc(1) NeuAc(1) of less than 100; or 5) a ratio of Hex(2) HexNAc(1): Hex (4) NeuAc(2) NeuGc(1) of greater than 10; and/or wherein the complex oligosaccharide comprises a plurality of oligosaccharides with 3 to 10 residues (DP3-10 oligosaccharides);

wherein at least one of the oligosaccharide has a Type I core; and/or wherein at least one of the oligosaccharide has a Type II core.

10. The composition of claim 7, wherein the complex oligosaccharide is at least 20% of the weight of the composition;

wherein the complex oligosaccharide is at least 50% of the weight of the composition;

wherein the complex oligosaccharide is at least 80% of the weight of the composition;

wherein fucosyllactose and/or sialyllactose comprises 1-5% of the total oligosaccharides;

wherein fucosyllactose and/or sialyllactose comprises 5-20% of the total oligosaccharides;

wherein fucosyllactose and/or sialyllactose comprises 20-50% of the total oligosaccharides;

wherein the mass ratio of the complex oligosaccharide to fucosyllactose and/or sialyllactose is from 20:1 to 1:10;

wherein the composition provides a total dietary intake of oligosaccharide in an amount of 0.001-100 grams per day;

wherein the oligosaccharide is in an amount of 1-20 grams, 3-20 grams, or 5-10 grams; and/or wherein the oligosaccharide is in an amount of 10, 15, 20, 25, 30, 35, 40, 45, or 50 grams.

11. The composition of claim 7, wherein the complex oligosaccharide comprises a plant-derived oligosaccharide;

wherein the plant oligosaccharide is from carrots, peas, broccoli, onions, tomatoes, peppers, rice, wheat, oats, bran, oranges, cocoa, olives, apples, grapes, sugar beets, cabbage, corn, or a mixture thereof;

wherein the plant oligosaccharide is from orange peels, cocoa hulls, olive pomace, tomato skins, grape pomace, corn silage, or a mixture thereof; and/or wherein the plant-derived oligosaccharides are between 2 and 10 sugar residues (DP2-DP10), between 3 and 10 sugar residues (DP3-DP10), between 5 and 10 sugar resides (DP5-DP10), or up to DP20.

12. The composition of claim 1, wherein the composition further comprises galactooligosaccharide (GOS);

wherein the composition further comprises a protein source rich in threonine, N-acetyl-threonine, gamma-glutamylthreonine, or a combination thereof; and/or wherein the composition further comprises a secondary metabolite.

13. The composition of claim 1, wherein the dry powder is spray dried or freeze-dried; and/or wherein the composition is freeze-dried in the presence of a suitable cryoprotectant.

14. The composition of claim 1, wherein the composition further comprises a cryoprotectant; wherein the cryoprotectant is glucose, lactose, raffinose, sucrose, trehalose, adonitol, glycerol, mannitol, methanol, polyethylene glycol, propylene glycol, ribitol, alginate, bovine serum albumin, carnitine, citrate, cysteine, dextran, dimethyl sulphoxide, sodium glutamate, glycine betaine, glycogen, hypotaurine, peptone, polyvinyl pyrrolidone, or taurine, mammalian milk oligosaccharides, chitin, chitosan, other polysaccharides, or a combination thereof.

15. The composition of claim 1, further comprising a stabilizer;

wherein the stabilizer is a flow agent or a milk protein.

16. The composition of claim 1, wherein the composition is a powder with a water activity level of less than 0.35, less than 0.30, less than 0.25, less than 0.2, or less than 0.1;

wherein the composition is an anhydrous composition;

wherein the composition is suspended in an oil; and/or wherein the composition is suspended in syrup having oligosaccharide at least 57% where water activity is low enough to keep *Bifidobacterium* dormant.

17. The composition of claim 16, wherein the oil is a medium chain triglyceride.

18. The composition of claim 1, wherein the composition is in the form of a packet, sachet, orally disintegrating tablet, foodstuff, capsule, lozenge, effervescent tablet, suppository, enema, capsule, dry powder, dry powder suspended in an oil, chewable composition, syrup, or gel;

wherein the capsule or tablet has an enteric coating;

wherein the enteric coating comprises one or more of fatty acids, waxes, shellac, plastics, plant fibers, methyl acrylate-methacrylic acid copolymers, cellulose acetate succinate, hydroxy propyl methyl cellulose phthalate, hydroxy propyl methyl cellulose acetate succinate, polyvinyl acetate phthalate (PVAP), methyl methacrylate-methacrylic acid copolymers, cellulose acetate trimellitate, sodium alginate, and zein;

wherein the composition is a pharmaceutical composition, dietary supplement, nutritional product, food product, probiotic, and/or prebiotic; and/or wherein the composition is formulated as a unit dose medicament.

* * * * *